(12) United States Patent
Shimuta

(10) Patent No.: US 10,111,592 B2
(45) Date of Patent: Oct. 30, 2018

(54) BIOSENSOR

(71) Applicant: Murata Manufacturing Co., Ltd., Nagaokakyo-shi, Kyoto-fu (JP)

(72) Inventor: Toru Shimuta, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 157 days.

(21) Appl. No.: 15/141,058

(22) Filed: Apr. 28, 2016

(65) Prior Publication Data
US 2016/0235310 A1  Aug. 18, 2016

Related U.S. Application Data

(63) Continuation of application No. 14/172,213, filed on Feb. 4, 2014, now Pat. No. 9,439,569, which is a (Continued)

(30) Foreign Application Priority Data

Aug. 19, 2011  (JP) .................................. 2011-179985

(51) Int. Cl.
*A61B 5/0205* (2006.01)
*A61B 5/00* (2006.01)
*A61B 5/0245* (2006.01)
*A61B 5/0408* (2006.01)
*A61B 5/0478* (2006.01)
(Continued)

(52) U.S. Cl.
CPC .......... *A61B 5/0059* (2013.01); *A61B 5/0205* (2013.01); *A61B 5/0245* (2013.01);
(Continued)

(58) Field of Classification Search
CPC ... A61B 5/0059; A61B 5/0205; A61B 5/0245; A61B 5/0408; A61B 5/0478;
(Continued)

(56) References Cited

U.S. PATENT DOCUMENTS 5,146,102 A * 9/1992 Higuchi ............... A61B 5/1172
250/227.11
5,444,520 A    8/1995 Murano
(Continued)

FOREIGN PATENT DOCUMENTS

EP     1 810 813 A1    7/2007
EP      1993148 A1    11/2008
(Continued)

*Primary Examiner* — Seung C Sohn
(74) *Attorney, Agent, or Firm* — Arent Fox LLP

(57) ABSTRACT

A biosensor includes light emitting elements and a light receiving element disposed on a principal surface of a wiring board; a light shielding portion disposed between a light-emitting-element sealing portion and a light-receiving-element sealing portion; a base medium having light transmitting properties, disposed in parallel with the wiring board with the light shielding portion therebetween; an adhesion layer having light transmitting properties, configured to bond the base medium with the light-emitting-element sealing portion, the light-receiving-element sealing portion, and the light shielding portion; and a first electrocardiograph electrode attached to a principal surface of the base medium. The refractive index of the base medium is set to be higher than that of the adhesion layer, and a surface of the first electrocardiograph electrode which is adjacent to the base medium is roughened so that stray light passing through the base medium will be scattered.

20 Claims, 17 Drawing Sheets

Related U.S. Application Data continuation of application No. PCT/JP2012/005063, filed on Aug. 9, 2012.

(51) Int. Cl.
*A61B 5/0492* (2006.01)
*A61B 5/1455* (2006.01)

(52) U.S. Cl.
CPC .......... *A61B 5/0408* (2013.01); *A61B 5/0478* (2013.01); *A61B 5/0492* (2013.01); *A61B 5/1455* (2013.01); *A61B 5/14551* (2013.01); *A61B 5/6826* (2013.01)

(58) Field of Classification Search
CPC . A61B 5/0492; A61B 5/1455; A61B 5/14551; A61B 5/6826
USPC ....................................................... 250/556
See application file for complete search history.

(56) References Cited

U.S. PATENT DOCUMENTS

| | | |
|---|---|---|
| 6,091,497 A | 7/2000 | Paritsky et al. |
| 6,491,639 B1 | 12/2002 | Turcott |
| 7,026,654 B2 | 4/2006 | Igaki |
| 2001/0042847 A1 | 11/2001 | Eisen et al. |
| 2004/0252867 A1* | 12/2004 | Lan ...................... G06K 9/0004 382/124 |
| 2009/0156912 A1 | 6/2009 | Kuhn et al. |
| 2009/0202251 A1 | 8/2009 | Shibayama |
| 2010/0056887 A1 | 3/2010 | Kimura et al. |
| 2011/0260176 A1 | 10/2011 | Onoe et al. |
| 2012/0071734 A1 | 3/2012 | Shimuta et al. |

FOREIGN PATENT DOCUMENTS

| | | | |
|---|---|---|---|
| EP | | 2087837 A1 | 8/2009 |
| EP | | 2 277 440 A1 | 1/2011 |
| EP | | 2 425 768 A1 | 3/2012 |
| JP | | H06-029504 | 2/1994 |
| JP | | 2000-075155 A | 3/2000 |
| JP | | 2006-158974 A | 6/2006 |
| JP | | 2011-096203 A | 5/2011 |
| JP | | 2013-000378 A | 1/2013 |
| WO | WO | 2007/097240 A1 | 8/2007 |
| WO | WO | 2008/065699 A1 | 6/2008 |
| WO | WO | 2010/125705 A1 | 11/2010 |

* cited by examiner

BIOSENSOR

CROSS-REFERENCE TO RELATED APPLICATIONS

The present application is a continuation of U.S. patent application Ser. No. 14/172,213, filed Feb. 4, 2014, which is a continuation of PCT/JP2012/005063 filed Aug. 9, 2012, which claims priority to Japanese Patent Application No. 2011-179985, filed Aug. 19, 2011, the entire contents of each of which are incorporated herein by reference.

TECHNICAL FIELD OF THE INVENTION

The present invention relates to a biosensor which obtains biological signals.

BACKGROUND OF THE INVENTION

These days, people are more and more concerned about health care and health maintenance and promotion. It is thus desirable that people can more easily obtain biological information, such as the pulse and electrocardiograms. Pulse monitors or pulse oximeters are known. More specifically, in such devices, by utilizing characteristics in which hemoglobin within the blood absorbs light in a range from visible light to infrared light, a change in the intensity of light passing through or reflected by a body, such as a finger, is obtained as a photoplethysmographic signal.

Patent Document 1 discloses a biological information monitoring sensor which serves both as a body electrode and an oximeter probe. By using this biological information monitoring sensor, taking of an electrocardiogram and measuring of oxygen saturation of hemoglobin within the blood can be performed simultaneously. More specifically, this biological information monitoring sensor includes an electrode element attached on a polymer film, an LED, which serves as a light emitting element, and a PD, which serves as a light receiving element, fixed on the electrode element with a predetermined spacing between the LED and the PD, and AMPS, which serves as a transparent conductive gel, for covering the elements. With this configuration, when the sensor contacts the skin surface of a body, the electrode element is brought into contact with the skin via the conductive AMPS, and thus, the function as a normal electrode element can be obtained. Meanwhile, the LED and the PD are in contact with the skin via the transparent AMPS, and thus, the function as an oximeter probe can be obtained.

Patent Document 1: Japanese Unexamined Utility Model Registration Application Publication No. 6-29504

As stated above, in the biological information monitoring sensor disclosed in Patent Document 1, the light emitting element (LED) and the light receiving element (PD) are covered with the transparent conductive gel (AMPS), and the LED and the PD contact a body skin via the transparent AMPS. Accordingly, when monitoring is performed, part of light emitted from the LED (detection light) may directly reach the PD via the transparent AMPS. Normally, the intensity of light (stray light) emitted from the LED and reaching the PD without passing through or being reflected by a body is higher than the intensity of light passing through or being reflected by a body. Thus, light to be detected, that is, light passing through or being reflected by a body, is embedded in stray light (noise), which may decrease the S/N ratio.

SUMMARY OF THE INVENTION

The present invention has been made in order to solve the above-described problem. It is an object of the present invention to provide a biosensor which obtains photoplethysmographic signals and which is capable of reducing the amount of stray light which is received without passing through a body.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; a base medium having light transmitting properties, disposed in parallel with the wiring board with the light shielding portion therebetween; an adhesion layer having light transmitting properties, disposed between the base medium and the light shielding portion and/or the light-emitting-element sealing portion and the light-receiving-element sealing portion, and configured to bond the base medium with the light shielding portion and/or the light-emitting-element sealing portion and the light-receiving-element sealing portion; and a plane electrode attached to a principal surface of the base medium such that the plane electrode overlaps neither of the light emitting element nor the light receiving element when viewed from a direction normal to the principal surface of the wiring board, and configured to monitor a potential of a body. The refractive index of the base medium is set to be higher than that of the adhesion layer, and the surface of the plane electrode which is adjacent to the base medium is roughened so that light passing through the base medium will be scattered.

In the biosensor according to the present invention, when a body, such as a fingertip, contacts the front surface of the plane electrode, light emitted from the light emitting element impinges on the body via the light-emitting-element sealing portion, the adhesion layer, and the base medium. Then, light passing through the body is received by the light receiving element via the base medium, the adhesion layer, and the light-receiving-element sealing portion. With this operation, a photoplethysmographic signal indicating a pulse wave of the body is obtained. Simultaneously, the potential of the body which is in contact with the plane electrode is detected by the plane electrode.

In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. Meanwhile, part of light emitted from the light emitting element enters the adhesion layer and the base medium and advances within the adhesion layer and the base medium toward the light receiving element. In the biosensor according to the present invention, however, the refractive index of the base medium is set to be higher than that of the adhesion layer, and also, the surface of the plane electrode adjacent to the base medium is roughened so that light passing through the base medium will be scattered. Accordingly, light (stray light) which has entered the adhesion layer and the base medium advances within the base medium having a higher refractive index while being reflected at the boundary between the base medium and the adhesion layer.

In this case, due to the formation of the rough surface of the plane electrode adjacent to the base medium, stray light advancing within the base medium is scattered by this surface, thereby reducing the amount of stray light which enters the light receiving element. As a result, in the biosensor which obtains a photoplethysmographic signal, it is possible to reduce the amount of stray light which is received without passing through a body.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; a base medium having light transmitting properties, disposed in parallel with the wiring board with the light shielding portion therebetween; an adhesion layer having light transmitting properties, disposed between the base medium and the light shielding portion and/or the light-emitting-element sealing portion and the light-receiving-element sealing portion, and configured to bond the base medium with the light shielding portion and/or the light-emitting-element sealing portion and the light-receiving-element sealing portion; and a plane electrode attached to a principal surface of the base medium such that the plane electrode overlaps neither of the light emitting element nor the light receiving element when viewed from a direction normal to the principal surface of the wiring board, and configured to monitor a potential of a body. The refractive index of the adhesion layer is set to be higher than that of the base medium, and the surface of the light shielding portion which is adjacent to the adhesion layer is roughened so that light passing through the adhesion layer will be scattered.

In the biosensor according to the present invention, when a body, such as a fingertip, contacts the front surface of the plane electrode, light emitted from the light emitting element impinges on the body via the light-emitting-element sealing portion, the adhesion layer, and the base medium. Then, light passing through or reflected by the body is received by the light receiving element via the base medium, the adhesion layer, and the light-receiving-element sealing portion. With this operation, a photoplethysmographic signal indicating a pulse wave of the body is obtained. Simultaneously, the potential of the body which is in contact with the plane electrode is detected by the plane electrode.

In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. Meanwhile, part of light emitted from the light emitting element enters the adhesion layer and the base medium and advances within the adhesion layer and the base medium toward the light receiving element. In the biosensor according to the present invention, however, the refractive index of the adhesion layer is set to be higher than that of the base medium, and also, the surface of the light shielding portion adjacent to the adhesion layer is roughened so that light passing through the adhesion layer will be scattered. Accordingly, light (stray light) which has entered the adhesion layer and the base medium advances within the adhesion layer having a higher refractive index while being reflected at the boundary between the adhesion layer and the base medium. In this case, due to the formation of the rough surface of the light shielding portion adjacent to the adhesion layer, stray light advancing within the adhesion layer is scattered by this surface, thereby reducing the amount of stray light which enters the light receiving element. As a result, in the biosensor which obtains a photoplethysmographic signal, it is possible to reduce the amount of stray light which is received without passing through a body.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; a base medium having light transmitting properties, disposed in parallel with the wiring board with the light shielding portion therebetween; an adhesion layer having light transmitting properties, disposed between the base medium and the light shielding portion and/or the light-emitting-element sealing portion and the light-receiving-element sealing portion, and configured to bond the base medium with the light shielding portion and/or the light-emitting-element sealing portion and the light-receiving-element sealing portion; and a plane electrode attached to a principal surface of the base medium such that the plane electrode overlaps neither of the light emitting element nor the light receiving element when viewed from a direction normal to the principal surface of the wiring board, and configured to monitor a potential of a body. The adhesion layer is at least partially divided into a portion closer to the light emitting element and a portion closer to the light receiving element.

In the biosensor according to the present invention, when a body, such as a fingertip, contacts the front surface of the plane electrode, light emitted from the light emitting element impinges on the body via the light-emitting-element sealing portion, the adhesion layer, and the base medium. Then, light passing through or reflected by the body is received by the light receiving element via the base medium, the adhesion layer, and the light-receiving-element sealing portion. With this operation, a photoplethysmographic signal indicating a pulse wave of the body is obtained. Simultaneously, the potential of the body which is in contact with the plane electrode is detected by the plane electrode.

In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. Meanwhile, part of light emitted from the light emitting element enters the adhesion layer and the base medium and advances within the adhesion layer and the base medium toward the light receiving element. In the biosensor according to the present invention, however, the adhesion layer is at least partially divided into a portion closer to the light emitting element and a portion closer to the light receiving element. Accordingly, stray light advancing within the adhesion layer in a direction from the light emitting element to the light receiving element is reflected or refracted on the end surfaces of the divided adhesion layer, thereby reducing the amount of stray light which passes through the adhesion layer and enters the light receiving element. As a result, in the biosensor which obtains a photoplethysmographic signal, it is possible to reduce the amount of stray light which is received without passing through a body.

In the biosensor according to the present invention, the adhesion layer may preferably be divided such that a minor angle between a direction in which the adhesion layer is divided and an imaginary straight line which passes through the adhesion layer and is parallel with a straight line connecting the light emitting element and the light receiving element is 50° or smaller.

With this configuration, since the adhesion layer is divided such that the angle (minor angle) between the direction in which the adhesion layer is divided and the imaginary straight line is 50° or smaller, the reflectance of light reflected at the divided end surfaces is increased. It is thus possible to further reduce the amount of stray light which is received through the adhesion layer.

In the biosensor according to the present invention, the adhesion layer may preferably be fully divided into a portion closer to the light emitting element and a portion closer to the light receiving element.

In this case, since the adhesion layer is fully divided into a portion positioned closer to the light emitting element and a portion closer to the light receiving element, the amount of reflected or refracted light is increased compared to a case in which the adhesion layer is only partially divided. It is thus possible to further reduce the amount of stray light which does not pass through a body and which is received through the adhesion layer.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; a base medium having light transmitting properties, disposed in parallel with the wiring board with the light shielding portion therebetween; an adhesion layer having light transmitting properties, disposed between the base medium and the light shielding portion and/or the light-emitting-element sealing portion and the light-receiving-element sealing portion, and configured to bond the base medium with the light shielding portion and/or the light-emitting-element sealing portion and the light-receiving-element sealing portion; and a plane electrode attached to a principal surface of the base medium such that the plane electrode overlaps neither of the light emitting element nor the light receiving element when viewed from a direction normal to the principal surface of the wiring board, and configured to monitor a potential of a body. The light transmittance of the adhesion layer is lower than the light transmittance of the base medium.

In the biosensor according to the present invention, when a body, such as a fingertip, contacts the front surface of the plane electrode, light emitted from the light emitting element impinges on the body via the light-emitting-element sealing portion, the adhesion layer, and the base medium. Then, light passing through or reflected by the body is received by the light receiving element via the base medium, the adhesion layer, and the light-receiving-element sealing portion. With this operation, a photoplethysmographic signal indicating a pulse wave of the body is obtained. Simultaneously, the potential of the body which is in contact with the plane electrode is detected by the plane electrode.

In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. Meanwhile, part of light emitted from the light emitting element enters the adhesion layer and the base medium and advances within the adhesion layer and the base medium toward the light receiving element. In the biosensor according to the present invention, however, the light transmittance of the adhesion layer is set to be lower than that of the base medium. Accordingly, stray light which has entered the adhesion layer attenuates more intently as it propagates in a direction from the light emitting element to the light receiving element, thereby reducing the amount of stray light which enters the light receiving element. As a result, in the biosensor which obtains a photoplethysmographic signal, it is possible to reduce the amount of stray light which is received without passing through a body.

In the biosensor according to the present invention, the adhesion layer may preferably be constituted by double-sided tape including a strip-like core member made of paper or nonwoven fabric and adhesive layers formed on both sides of the core member.

In this case, the core member forming the adhesion layer is made of paper or nonwoven fabric. This makes it relatively easy for light to pass in the thickness direction of the core member and relatively difficult for light to pass in the longitudinal direction of the core member. Thus, it is possible to allow light which is emitted from the light emitting element and which will impinge on a body and light which has passed through the body and which will impinge on the light receiving element to pass through the core member, and to reduce stray light propagating through the core member in a direction from the light emitting element to the light receiving element. Accordingly, it is possible to reduce the amount of stray light which does not pass through a body and which is received through the adhesion layer.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; and a cover having light transmitting properties, disposed in parallel with the wiring board with the light shielding portion therebetween. The bottom surface and/or the top surface of the cover is roughened so that light passing through the cover will be scattered.

In the biosensor according to the present invention, when a body, such as a fingertip, contacts the front surface of the cover, light emitted from the light emitting element impinges on the body via the light-emitting-element sealing portion and the cover. Then, light passing through the body is received by the light receiving element via the cover and the light-receiving-element sealing portion. With this operation, a photoplethysmographic signal indicating a pulse wave of the body is obtained. In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. Meanwhile, part of light emitted from the light emitting element enters the cover and propagates through the cover toward the light receiving element. In the biosensor according to the present invention, however, the bottom surface and/or the top surface of the cover is roughened so that stray light passing through the cover is scattered. Accordingly, light (stray light) which has entered the cover is scattered when advancing within the cover while being reflected, thereby reducing the amount of stray light which enters the light receiving element. As a result, in the biosensor which obtains a photoplethysmographic signal, it is possible to reduce the amount of stray light which is received without passing through a body.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; and a cover having light transmitting properties, disposed in parallel with the wiring board with the light shielding portion therebetween. The cover is at least partially divided into a portion closer to the light emitting element and a portion closer to the light receiving element.

In the biosensor according to the present invention, when a body, such as a fingertip, contacts the front surface of the cover, light emitted from the light emitting element impinges on the body via the light-emitting-element sealing portion and the cover. Then, light passing through or reflected by the body is received by the light receiving element via the cover and the light-receiving-element sealing portion. With this operation, a photoplethysmographic signal indicating a pulse wave of the body is obtained. In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. Meanwhile, part of light emitted from the light emitting element enters the cover and propagates through the cover toward the light receiving element. In the biosensor according to the present invention, however, the cover is at least partially divided into a portion closer to the light emitting element and a portion closer to the light receiving element. Accordingly, stray light advancing within the cover in a direction from the light emitting element to the light receiving element is reflected or refracted at the end surfaces of the divided cover, thereby reducing the amount of stray light which enters the light receiving element through the cover. As a result, in the biosensor which obtains a photoplethysmographic signal, it is possible to reduce the amount of stray light which is received without passing through a body.

In the biosensor according to the present invention, the cover may preferably be divided such that a minor angle between a direction in which the cover is divided and an imaginary straight line which passes through the cover and is parallel with a straight line connecting the light emitting element and the light receiving element is 50° or smaller.

With this configuration, since the cover is divided such that the angle (minor angle) between the direction in which the cover is divided and the imaginary straight line is 50° or smaller, the reflectance of light reflected at the divided end surfaces is increased. It is thus possible to further reduce the amount of stray light which is received through the cover.

In the biosensor according to the present invention, the cover may preferably be fully divided into a portion closer to the light emitting element and a portion closer to the light receiving element.

In this embodiment, since the cover is fully divided into a portion closer to the light emitting element and a portion closer to the light receiving element, the amount of reflected or refracted light is increased compared to a case in which the cover is only partially divided. It is thus possible to further reduce the amount of stray light which does not pass through a body and which is received through the cover.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; and a cover having light transmitting properties, disposed in parallel with the wiring board with the light shielding portion therebetween. A plurality of grooves are formed on a bottom surface and/or a top surface of the cover in a direction which intersects with an imaginary straight line which passes through the cover and is parallel with a straight line connecting the light emitting element and the light receiving element.

In the biosensor according to the present invention, when a body, such as a fingertip, contacts the front surface of the cover, light emitted from the light emitting element impinges on the body via the light-emitting-element sealing portion and the cover. Then, light passing through the body is received by the light receiving element via the cover and the light-receiving-element sealing portion. With this operation, a photoplethysmographic signal indicating a pulse wave of the body is obtained. In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. Meanwhile, part of light emitted from the light emitting element enters the cover and propagates through the cover toward the light receiving element. In the biosensor according to the present invention, however, a plurality of grooves are formed on a bottom surface and/or a top surface of the cover in a direction which intersects with an imaginary straight line which passes through the cover and is parallel with a straight line connecting the light emitting element and the light receiving element. Accordingly, light (stray light) which has entered the cover strikes the lateral surfaces of the plurality of grooves when advancing within the cover while being reflected, and is radiated from the lateral surfaces to the exterior, thereby reducing the amount of stray light which enters the light receiving element. As a result, in the biosensor which obtains a photoplethysmographic signal, it is possible to reduce the amount of stray light which is received without passing through a body.

In the biosensor according to the present invention, the aspect ratio of a region between the grooves may preferably be set to be one or greater.

If the aspect ratio is decreased (if the depth of the grooves is decreased), it is less likely that light (stray light) will strike the lateral surfaces of the grooves, and thus, the amount of light which strikes the bottom surfaces of the grooves, is reflected thereon, and returns is increased. In this case, however, the aspect ratio is set to be one or greater. This makes it easier for light (stray light) to strike the lateral surfaces of the grooves, thereby making it possible to further reduce the amount of stray light which enters the light receiving element.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; a base medium having light transmitting properties, disposed in parallel with the wiring board with the light shielding portion therebetween; and an adhesion layer having light transmitting properties, disposed between the base medium and the light shielding portion and/or the light-emitting-element sealing portion and the light-receiving-element sealing portion, and configured to bond the base medium with the light shielding portion and/or the light-emitting-element sealing portion and the light-receiving-element sealing portion. The refractive index of the adhesion layer is set to be higher than that of the base medium, and the surface of the light shielding portion which is adjacent to the adhesion layer is roughened so that light passing through the adhesion layer will be scattered.

In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. Meanwhile, part of light emitted from the light emitting element enters the adhesion layer and the base medium and advances within the adhesion layer and the base medium toward the light receiving element. In the biosensor according to the present invention, however, the refractive index of the adhesion layer is set to be higher than that of the base medium, and also, the surface of the light shielding portion adjacent to the adhesion layer is roughened so that light passing through the adhesion layer will be scattered. Accordingly, light (stray light) which has entered the adhesion layer and the base medium advances within the adhesion layer having a higher refractive index while being reflected at the boundary between the adhesion layer and the base medium. In this case, due to the formation of the rough surface of the light shielding portion adjacent to the adhesion layer, stray light advancing within the adhesion layer is scattered by this surface, thereby reducing the amount of stray light which enters the light receiving element. As a result, in the biosensor which obtains a photoplethysmographic signal, it is possible to reduce the amount of stray light which is received without passing through a body.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; a base medium having light transmitting properties, disposed in parallel with the wiring board with the light shielding portion therebetween; and an adhesion layer having light transmitting properties, disposed between the base medium and the light shielding portion and/or the light-emitting-element sealing portion and the light-receiving-element sealing portion, and configured to bond the base medium with the light shielding portion and/or the light-emitting-element sealing portion and the light-receiving-element sealing portion. The adhesion layer is at least partially divided into a portion closer to the light emitting element and a portion closer to the light receiving element.

In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. Meanwhile, part of light emitted from the light emitting element enters the adhesion layer and the base medium and advances within the adhesion layer and the base medium toward the light receiving element. In the biosensor according to the present invention, however, the adhesion layer is at least partially divided into a portion closer to the light emitting element and a portion closer to the light receiving element. Accordingly, stray light advancing within the adhesion layer in a direction from the light emitting element to the light receiving element is reflected or refracted on the end surfaces of the divided adhesion layer, thereby reducing the amount of stray light which enters the light receiving element. As a result, in the biosensor which obtains a photoplethysmographic signal, it is possible to reduce the amount of stray light which is received without passing through a body.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; a base medium having light transmitting properties, disposed in parallel with the wiring board with the light shielding portion therebetween; and an adhesion layer having light transmitting properties, disposed between the base medium and the light shielding portion and/or the light-emitting-element sealing portion and the light-receiving-element sealing portion, and configured to bond the base medium with the light shielding portion and/or the light-emitting-element sealing portion and the light-receiving-element sealing portion. The light transmittance of the adhesion layer is lower than that of the base medium.

In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. Meanwhile, part of light emitted from the light emitting element enters the adhesion layer and the base medium and advances within the adhesion layer and the base medium toward the light receiving element. In the biosensor according to the present invention, however, the light transmittance of the adhesion layer is set to be lower than that of the base medium. Accordingly, stray light which has entered the adhesion layer attenuates more intently as it propagates in a direction from the light emitting element to the light receiving element, thereby reducing the amount of stray light which enters the light receiving element. As a result, in the biosensor which obtains a photoplethysmographic signal, it is possible to reduce the amount of stray light which is received without passing through a body.

According to the present invention, in a biosensor which obtains photoplethysmographic signals, it is possible to reduce the amount of stray light which is received without passing through a body.

DETAILED DESCRIPTION OF THE PREFERRED EMBODIMENTS

Figure 1:
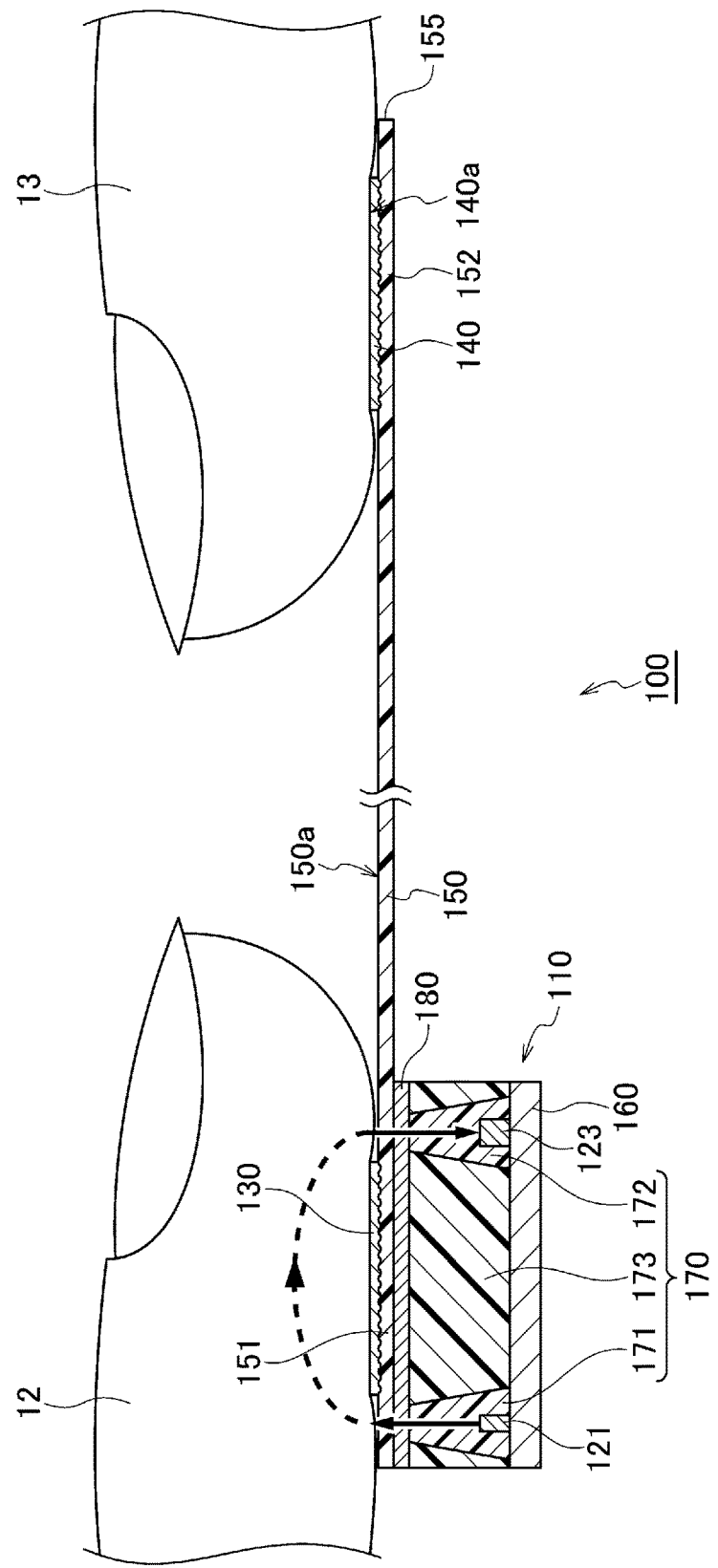
FIG. 1 is a longitudinal sectional view of a biosensor according to a first embodiment.

A preferred embodiment of the present invention will be described below with reference to the drawings. In the drawings, the same elements are designated by like reference numerals, and an explanation of the same element will be given only once.

(First Embodiment)

Figure 2:
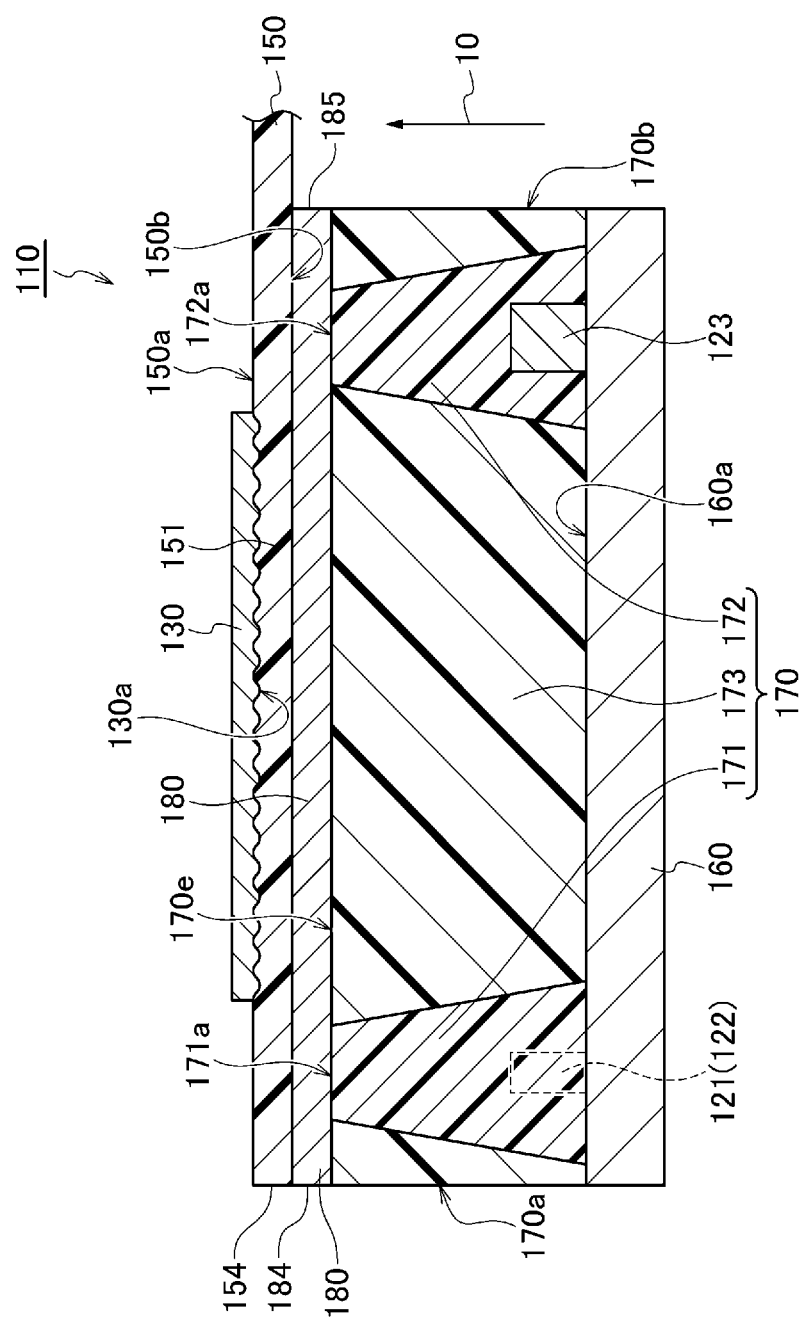
FIG. 2 is a longitudinal sectional view of a sensor unit forming the biosensor according to the first embodiment.
Figure 3:
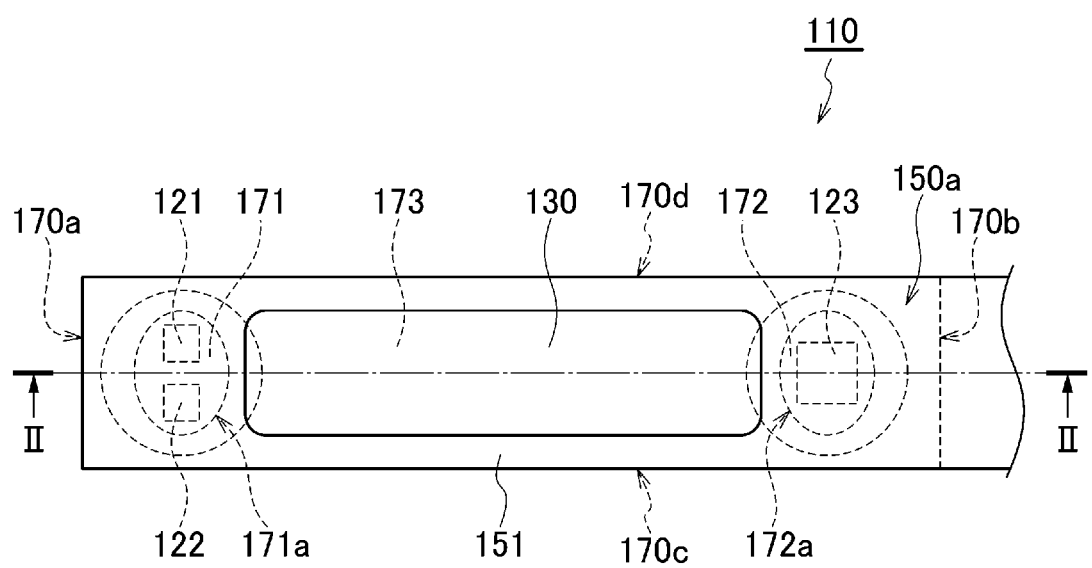
FIG. 3 is a plan view of the sensor unit.

The configuration of a biosensor 100 according to a first embodiment will be described below with reference to FIGS. 1 through 3. FIG. 1 is a longitudinal sectional view of the biosensor 100. FIG. 2 is a longitudinal sectional view of a sensor unit 110 forming the biosensor 100. In FIG. 2, a sectional view taken along line II-II in FIG. 3 is shown. FIG. 3 is a plan view of the sensor unit 110.

The biosensor 100 is a sensor which performs simultaneous detection (monitoring) of items of biological information upon a fingertip touching the biosensor 100, for example, taking of an electrocardiogram and measuring of the pulse and oxygen saturation are performed at the same time. The biosensor 100 optically measures the pulse and oxygen saturation by utilizing absorption characteristics of hemoglobin within the blood, and at the same time, it electrically monitors a change in the potential generated in accordance with the activity of the heart (takes an electrocardiogram) by using two electrodes 130 and 140.

In order to implement this function, the biosensor 100 includes two light emitting elements 121 and 122, a light receiving element 123, a first electrocardiograph electrode 130, a second electrocardiograph electrode 140, a base medium 150, a wiring board 160, a sealing section 170, and an adhesion layer 180.

The base medium 150 is formed in a strip-like shape. The first and second electrocardiograph electrodes 130 and 140 are disposed on a principal surface 150a of the base medium 150. The first electrocardiograph electrode 130 is disposed in one end region 151 of the base medium 150, while the second electrocardiograph electrode 140 is disposed in the other end region 152. In the end region 151 of the base medium 150, the light emitting elements 121 and 122, the light receiving element 123, the wiring board 160, the sealing section 170, and the adhesion layer 180 are integrally formed, together with the first electrocardiograph electrode 130. Hereinafter, for the sake of convenience, this integrally formed unit will be referred to as the "sensor unit 110". This sensor unit 110 is formed generally in a rectangular parallelepiped. In FIGS. 1 and 2, the height is shown in a relatively enlarged dimension for representation.

The light emitting elements 121 and 122 and the light receiving element 123 are mounted on a principal surface 160a of the wiring board 160 formed in a rectangular shape. The light emitting elements 121 and 122 are disposed side by side on a shorter side of the wiring board 160 at one end portion of the principal surface 160a. Meanwhile, the light receiving element 123 is disposed at the other end portion of the principal surface 160a. The distance from the light emitting elements 121 and 122 to the light receiving element 123 is set to be, for example, about 4 to 20 mm.

The two light emitting elements 121 and 122 emit light beams of different wavelengths in order to obtain the ratio of oxyhemoglobin to deoxyhemoglobin indicating oxygen saturation within the blood. For example, the light emitting element 121 emits light around an infrared light range in which the absorption coefficient of oxyhemoglobin is high. The light emitting element 122 emits light around a red light range in which the absorption coefficient of deoxyhemoglobin is high.

As the light emitting elements 121 and 122, LED, VCSEL (Vertical Cavity Surface Emitting LASER), a resonator LED, or the like, may be used. As the light receiving element 123, a photodiode, a phototransistor, or the like, may be suitably used.

The sealing section 170 is formed in the shape of a rectangular parallelepiped on the principal surface 160a of the wiring board 160. The sealing section 170 includes a light-emitting-element sealing portion 171 for sealing the light emitting elements 121 and 122, a light-receiving-element sealing portion 172 for sealing the light receiving element 123, and a light shielding portion 173.

The light-emitting-element sealing portion 171 is formed from a translucent resin in the shape of a circular truncated cone and seals the light emitting elements 121 and 122. The light-receiving-element sealing portion 172 is formed from a translucent resin in the shape of a circular truncated cone and seals the light receiving element 123. As the translucent resin forming the light-emitting-element sealing portion 171 and the light-receiving-element sealing portion 172, a transparent epoxy resin, for example, is used.

The light shielding portion 173 is formed by filling a resin having light-shielding properties into a region between the light-emitting-element sealing portion 171 and the light-receiving-element sealing portion 172 and into a region around the light-emitting-element sealing portion 171 and the light-receiving-element sealing portion 172 on the principal surface 160a of the wiring board 160. The light shielding portion 173 defines four lateral surfaces 170a through 170d of the sealing section 170. As the light shielding portion 173, for example, an epoxy resin containing powder having light shielding properties, such as carbon black, is suitably used.

The top surfaces of the above-described light-emitting-element sealing portion 171, light-receiving-element sealing portion 172, and light shielding portion 173 define a top surface 170e of the sealing section 170. The end region 151 of the base medium 150 on which the first electrocardiograph electrode 130 is disposed is bonded to the top surface 170e of the sealing section 170 with the adhesion layer 180 therebetween. The adhesion layer 180 has the same shape and the same size as the top surface 170e of the sealing section 170 and overlaps the top surface 170e of the sealing section 170. That is, the adhesion layer 180 covers an opening 171a of the light-emitting-element sealing portion 171 and an opening 172a of the light-receiving-element sealing portion 172.

An end portion 184 of the adhesion layer 180 and an end portion 154 of the base medium 150 closer to the light emitting elements 121 and 122 are positioned farther outward (toward the lateral surface 170a) than the opening 171a of the light-emitting-element sealing portion 171. That is, the end portions 184 and 154 of the adhesion layer 180 and the base medium 150, respectively, are disposed such that they do not overlap the opening 171a when viewed from a direction 10 normal to the principal surface 160a of the wiring board 160.

An end portion 185 of the adhesion layer 180 closer to the light receiving element 123 is positioned farther outward (toward the lateral surface 170b) than the opening 172a of the light-receiving-element sealing portion 172. An end portion 155 of the base medium 150 is not positioned near the opening 172a of the light-receiving-element sealing portion 172. That is, the end portions 185 and 155 of the adhesion layer 180 and the base medium 150, respectively, are disposed such that they do not overlap the opening 172a when viewed from the direction 10 normal to the principal surface 160a.

As the adhesion layer 180, for example, double-sided tape without a core member, is suitably used. By means of the adhesion layer 180, a back side 150b of the base medium 150 is bonded to the opening 171a of the light-emitting-element sealing portion 171, the opening 172a of the light-receiving-element sealing portion 172, and the top surface of the light shielding section 170.

The adhesion layer 180 has light transmitting properties, and the base medium 150 also has light transmitting properties. The refractive index of the base medium 150 is set to be higher than that of the adhesion layer 180. As the adhesion layer 180, double-sided tape including a translucent core member made from polyimide or PET and adhesive layers formed on both sides of the core member may be used. In this case, the refractive index of the base medium 150 is set to be higher than that of the core member and that of the adhesive layers forming the adhesion layer 180.

The base medium 150 is formed from, for example, a material having a refractive index of about 1.5 to 1.6. More specifically, the base medium 150 is formed from polyimide, PET (polyethylene terephthalate), or the like. The adhesion layer 180 is formed from, for example, a material having a refractive index of about 1.4 to 1.45. The adhesion layer 180 is formed from, for example, an acrylic resin.

The first electrocardiograph electrode 130 is a plane electrode formed in the shape of a rectangular thin film, and is disposed in the end region 151 of the base medium 150. That is, the first electrocardiograph electrode 130 is disposed above the sealing section 170 used for sealing the light emitting elements 121 and 122 and the light receiving element 123.

The first electrocardiograph electrode 130 is disposed between the light emitting elements 121 and 122 and the light receiving element 123 on the principal surface 150a of the base medium 150 when viewed from the direction 10 normal to the principal surface 160a of the wiring board 160. Moreover, the electrocardiograph electrode 130 is disposed at a position at which it overlaps neither of the light emitting elements 121 and 122 nor the light receiving element 123 and at a position at which it overlaps neither of the opening 171a of the light-emitting-element sealing portion 171 nor the opening 172a of the light-receiving-element sealing portion 172 when viewed from the direction 10 normal to the principal surface 160a.

The first and second electrocardiograph electrodes 130 and 140 are each constituted by a metallic thin film formed by, for example, plating, thin-film/thick-film process, or rolling. The surfaces (for example, the back surfaces) of the first and second electrocardiograph electrodes 130 and 140 which are in contact with the base medium 150 are roughened by, for example, etching. The roughened surface of the first electrocardiograph electrode 130 will be referred to as a "rough surface 130a", and the roughened surface of the second electrocardiograph electrode 140 will be referred to as a "rough surface 140a". The back surface of the second electrocardiograph electrode 140 does not necessarily have to be roughened.

The detection of biological information by using the biosensor 100 is performed by allowing two different parts of a body, for example, a fingertip 12 of a left hand and a fingertip 13 of a right hand of a patient, to contact the biosensor 100, as shown in FIG. 1. In this case, the fingertip 12 of the left hand is in contact with the front surface of the first electrocardiograph electrode 130 and the principal surface 150a of the base medium 150 protruding from the periphery of the electrocardiograph electrode 130. The fingertip 13 of the right hand is in contact with the entire front surface of the second electrocardiograph electrode 140.

When detecting biological information, light emitted from the light emitting elements 121 and 122 passes through the light-emitting-element sealing portion 171 and impinges on the adhesion layer 180 through the opening 171a. Light then passes through the adhesion layer 180 and the base medium 150 and impinges on the fingertip 12.

Light incident on and passing through the fingertip 12 further passes through the base medium 150 and the adhesion layer 180 and impinges on the opening 172a of the light-receiving-element sealing portion 172. Then, light passes through the light-receiving-element sealing portion 172 and is received by the light receiving element 123. With this operation, a change in the intensity of light passing through the fingertip 12 is obtained as a photoplethysmographic signal. In this case, since light beams of different wavelengths are emitted from the two light emitting elements 121 and 122, the intensity of the transmitted light concerning the two wavelengths can be obtained.

At the same time as obtaining a photoplethysmographic signal, the potential of the fingertip 12 is obtained by the first electrocardiograph electrode 130, and the potential of the fingertip 13 is obtained by the second electrocardiograph electrode 140. That is, by using the biosensor 100, a photoplethysmographic signal and an electrocardiogram can be obtained simultaneously.

The adhesion layer 180 and the base medium 150 having light transmitting properties are disposed between the light emitting elements 121 and 122 and the fingertip 12. Accordingly, part of light emitted from the light emitting elements 121 and 122 enters the adhesion layer 180 and the base medium 150 and propagates through the adhesion layer 180 and the base medium 150 toward the light receiving element 123. In this biosensor 100, the refractive index of the base medium 150 is set to be higher than that of the adhesion layer 180, and the back surface 130a of the first electrocardiograph electrode 130 is roughened so that light passing through the base medium 150 may be scattered. Accordingly, light which has entered the adhesion layer 180 and the base medium 150 advances within the base medium 150 having a higher refractive index while being reflected at the boundary between the base medium 150 and the adhesion layer 180. In this case, since the back surface 130a of the first electrocardiograph electrode 130 is roughened, stray light which advances within the base medium 150 is scattered by the formation of the rough back surface 130a, thereby reducing the amount of stray light which enters the light receiving element 123.

As discussed above in detail, in the biosensor 100 according to this embodiment, when the fingertip 12 contacts the front surface of the first electrocardiograph electrode 130, light emitted from the light emitting elements 121 and 122 impinges on the fingertip 12 via the light-emitting-element sealing portion 171, the adhesion layer 180, and the base medium 150. Then, light passing through the fingertip 12 is received by the light receiving element 123 via the base medium 150, the adhesion layer 180, and the light-receiving-element sealing portion 172. With this operation, a photoplethysmographic signal indicating a pulse wave of the fingertip 12 is obtained. Simultaneously, the potential of the fingertip 12 which is in contact with the first electrocardiograph electrode 130 and the potential of the fingertip 13 which is in contact with the second electrocardiograph electrode 140 are detected.

In the biosensor 100, the light shielding portion 173 is disposed between the light-emitting-element sealing portion 171 and the light-receiving-element sealing portion 172. Accordingly, light emitted from the light emitting elements 121 and 122 is blocked from directly impinging on the light receiving element 123 by the provision of the light shielding portion 173. Meanwhile, light which has entered the adhesion layer 180 and the base medium 150 advances within the base medium 150 having a higher refractive index toward the light receiving element 123 while being reflected at the boundary between the base medium 150 and the adhesion layer 180. In this case, since the back surface 130a of the first electrocardiograph electrode 130 is roughened, stray light which advances within the base medium 150 is scattered by the formation of the rough back surface 130a, thereby reducing the amount of stray light which enters the light receiving element 123. As a result, in the biosensor 100 which simultaneously obtains a photoplethysmographic signal and potentials of the fingertips 12 and 13 (electrocardiogram), it is possible to reduce the amount of stray light which is received without passing through the fingertip 12.

Figure 4:
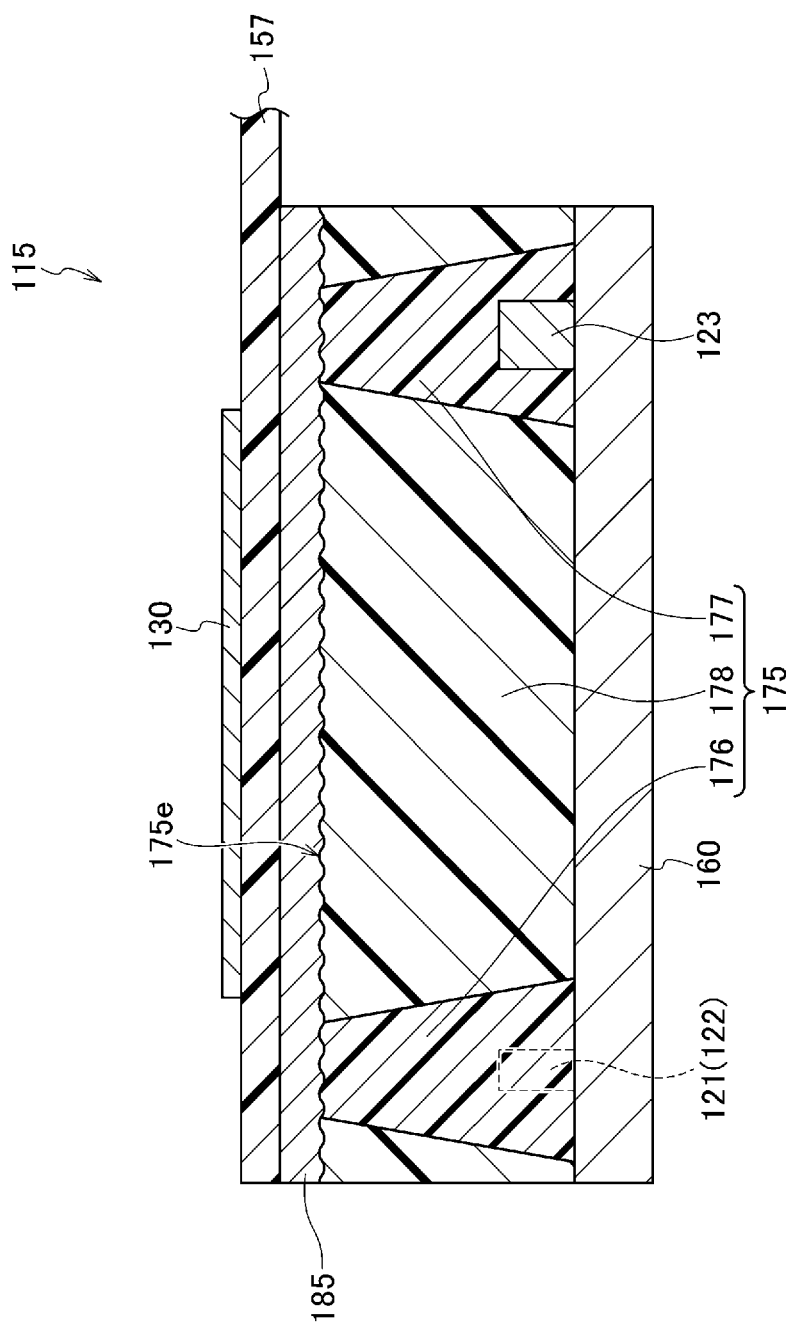
FIG. 4 is a longitudinal sectional view of a sensor unit forming a biosensor according to a modified example of the first embodiment.

A biosensor according to a modified example of the first embodiment will now be described below with reference to FIG. 4. FIG. 4 is a longitudinal sectional view of a sensor unit 115 forming a biosensor according to the modified example. In this modified example, the configuration of the sensor unit 115 different from that of the above-described sensor unit 110 will be principally described, and an explanation of the features and elements of the sensor unit 115 identical to or similar to those of the sensor unit 110 will be omitted.

The sensor unit 115 is different from the sensor unit 110 in that the refractive index of an adhesion layer 185 is set to be higher than that of a base medium 157. The base medium 157 is formed from polyimide or the like having a refractive index of about 1.4 to 1.45. The adhesion layer 185 is formed from an epoxy or acryl resin having a refractive index of about 1.45 to 1.6.

The sensor unit 115 is also different from the sensor unit 110 in that, instead of the back surface 130a of the first electrocardiograph electrode 130, a top surface 175e of a sealing section 175 is roughened so that stray light may be scattered. That is, in the sensor unit 115, top surfaces of a light-emitting-element sealing portion 176, a light-receiving-element sealing portion 177, and a light shielding portion 178 forming the sealing section 175 are roughened. Alternatively, only the top surface of the light shielding portion 178 may be roughened.

As in the above-described biosensor 100, in the biosensor according to this modified example, when a fingertip contacts the front surface of the first electrocardiograph electrode 130, light emitted from the light emitting elements 121 and 122 impinges on the fingertip via the light-emitting-element sealing portion 176, the adhesion layer 185, and the base medium 157. Then, light passing through the fingertip is received by the light receiving element 123 via the base medium 157, the adhesion layer 185, and the light-receiving-element sealing portion 177. With this operation, a photoplethysmographic signal indicating a pulse wave of the fingertip is obtained. Simultaneously, the potential of the fingertip which is in contact with the first electrocardiograph electrode 130 and the potential of a fingertip which is in contact with the second electrocardiograph electrode 140 (not shown) are detected.

In the sensor unit 115 forming the biosensor according to this modified example, the light shielding portion 178 is disposed between the light-emitting-element sealing portion 176 and the light-receiving-element sealing portion 177. Accordingly, light emitted from the light emitting elements 121 and 122 is blocked from directly impinging on the light receiving element 123 by the provision of the light shielding portion 178. Meanwhile, part of light emitted from the light emitting elements 121 and 122 enters the adhesion layer 185 and the base medium 157 and propagates within the adhesion layer 185 and the base medium 157 toward the light receiving element 123. In this case, in the sensor unit 115, since the refractive index of the adhesion layer 185 is set to be higher than that of the base medium 157, and also, the top surface 175e of the light-emitting-element sealing portion 176, the light-receiving-element sealing portion 177, and the light shielding portion 178 is roughened so that stray light propagating through the adhesion layer 185 may be scattered. Accordingly, light which has entered the adhesion layer 185 and the base medium 157 advances within the adhesion layer 185 having a higher refractive index while being reflected at the boundary between the adhesion layer 185 and the base medium 157. In this case, since the top surface 175e of the light-emitting-element sealing portion 176, the light-receiving-element sealing portion 177, and the light shielding portion 178 is roughened, stray light which advances within the adhesion layer 185 is scattered by the formation of the rough surface 175e, thereby reducing the amount of stray light which enters the light receiving element 123. As a result, in the biosensor which simultaneously obtains a photoplethysmographic signal and potentials of fingertips (electrocardiogram), it is possible to reduce the amount of stray light which is received without passing through a fingertip.

The first embodiment and a modified example thereof have been discussed above. However, the present invention is not restricted to the above-described embodiment, and various modifications may be made. For example, in the above-described embodiment, as the first and second electrocardiograph electrodes 130 and 140, a metallic thin film formed by, for example, plating, thin-film/thick-film process, or rolling, is used. However, the first and second electrocardiograph electrodes 130 and 140 may be formed by, for example, screen-printing a silver paste.

The shapes of the light-emitting-element sealing portions 171 and 176, the light-receiving-element sealing portions 172 and 177, and the light shielding portions 173 and 178 are not restricted to the above-described shapes. For example, the light shielding portion may be formed in a wall-like shape (planar shape). The light-emitting-element sealing portions 171 and 176 may be exposed to the lateral surface 170a of the sealing sections 170 and 175, respectively, on the side closer to the light emitting elements 121 and 122. Similarly, the light-receiving-element sealing portions 172 and 177 may be exposed to the lateral surface 170b of the sealing sections 170 and 175, respectively, on the side closer to the light receiving element 123.

Moreover, in the above-described embodiment, two light emitting elements are provided. However, one light emitting element may be provided, or three or more light emitting elements may be provided. In the above-described embodiment, the first and second electrocardiograph electrodes 130 and 140 are disposed on one base medium 150 or 157. However, the first and second electrocardiograph electrodes 130 and 140 may be disposed on different base mediums.

In the above-described first embodiment, the back surface 130a of the first electrocardiograph electrode 130 is roughened. Alternatively, instead of or in addition to making the back surface 130a of the first electrocardiograph electrode 130 rough, the back surface 150b of the base medium 150 may be roughened.

In the above-described modified example, a photoplethysmographic signal and an electrocardiogram are obtained simultaneously. However, if an electrocardiogram is not obtained, that is, only photoelectric pulse waves are measured, the provision of the first and second electrocardiograph electrodes 130 and 140 is not necessary, and thus, the first and second electrocardiograph electrodes 130 and 140 may be omitted.

(Second Embodiment)

Figure 5:
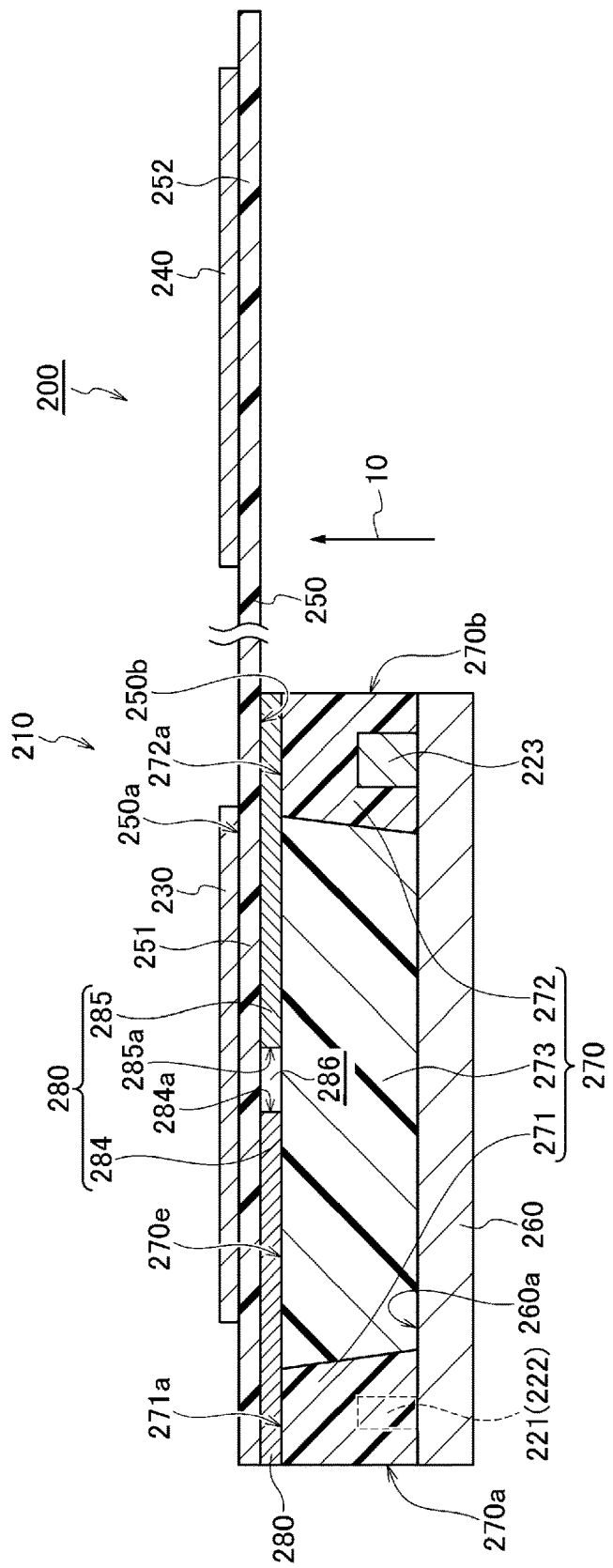
FIG. 5 is a longitudinal sectional view of a biosensor according to a second embodiment.
Figure 6:
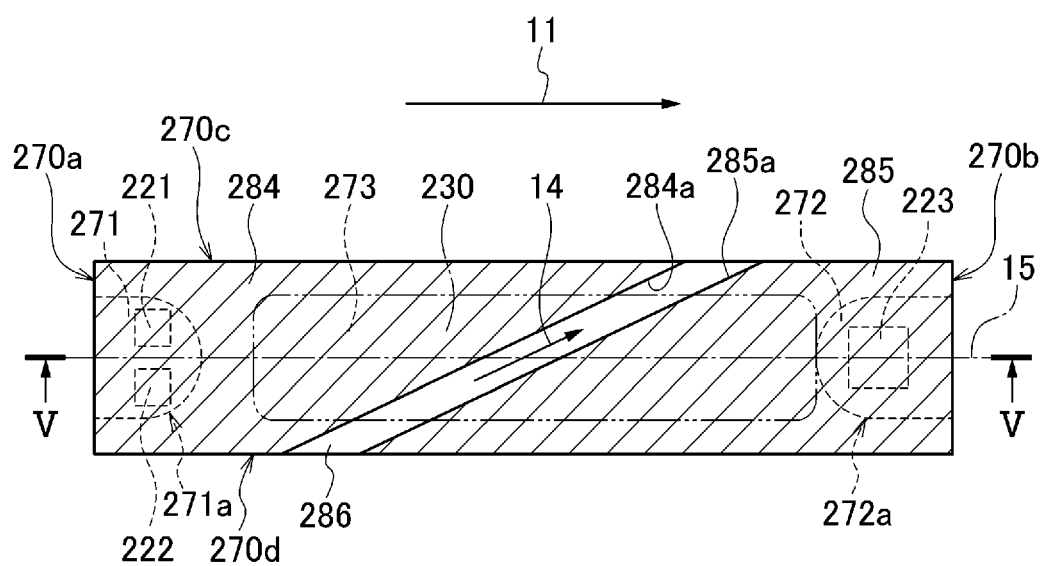
FIG. 6 is a plan view of a sensor unit forming the biosensor according to the second embodiment.

The configuration of a biosensor 200 according to a second embodiment will be described below with reference to FIGS. 5 and 6. Only a simple explanation will be given of the configuration of the biosensor 200 identical to or similar to that of the biosensor 100 of the first embodiment, and points different from those of the biosensor 100 will be principally described. FIG. 5 is a longitudinal sectional view of the biosensor 200. In FIG. 5, a sectional view taken along line V-V in FIG. 6 is shown. FIG. 6 is a plan view of a sensor unit 210 forming the biosensor 200.

The biosensor 200 is a sensor which performs simultaneous detection of items of biological information upon a fingertip touching the biosensor 200, for example, taking of an electrocardiogram and measuring of the pulse and oxygen saturation are performed at the same time. The biosensor 200 optically measures the pulse and oxygen saturation by utilizing absorption characteristics of hemoglobin within the blood, and at the same time, it electrically monitors a change in the potential generated in accordance with the activity of the heart (takes an electrocardiogram) by using two electrodes 230 and 240.

In order to implement this function, the biosensor 200 includes two light emitting elements 221 and 222, a light receiving element 223, a first electrocardiograph electrode 230, a second electrocardiograph electrode 240, a base medium 250, a wiring board 260, a sealing section 270, and an adhesion layer 280.

The base medium 250 is formed in a strip-like shape. The first and second electrocardiograph electrodes 230 and 240 are disposed on a principal surface 250a of the base medium 250. The first electrocardiograph electrode 230 is disposed in one end region 251 of the base medium 250, while the second electrocardiograph electrode 240 is disposed in the other end region 252. In the end region 251 of the base medium 250, the light emitting elements 221 and 222, the light receiving element 223, the wiring board 260, the sealing section 270, and the adhesion layer 280 are integrally formed, together with the first electrocardiograph electrode 230. Hereinafter, for the sake of convenience, this integrally formed unit will be referred to as the "sensor unit 210". This sensor unit 210 is formed generally in a rectangular parallelepiped. In FIG. 5, the height is shown in a relatively enlarged dimension for representation.

The light emitting elements 221 and 222 and the light receiving element 223 are mounted on a principal surface 260a of the wiring board 260 formed in a rectangular shape. The light emitting elements 221 and 222 are disposed side by side on a shorter side of the wiring board 260 at one end portion of the principal surface 260a. Meanwhile, the light receiving element 223 is disposed at the other end portion of the principal surface 260a. The distance from the light emitting elements 221 and 222 to the light receiving element 223 is set to be, for example, about 4 to 20 mm.

The two light emitting elements 221 and 222 emit light beams of different wavelengths in order to obtain the ratio of oxyhemoglobin to deoxyhemoglobin indicating oxygen saturation within the blood. For example, the light emitting element 221 emits light around an infrared light range in which the absorption coefficient of oxyhemoglobin is high. The light emitting element 222 emits light around a red light range in which the absorption coefficient of deoxyhemoglobin is high.

As the light emitting elements 221 and 222, LED, VCSEL, a resonator LED, or the like, may be used. As the light receiving element 223, a photodiode, a phototransistor, or the like, may be suitably used.

The sealing section 270 is formed in the shape of a rectangular parallelepiped on the principal surface 260a of the wiring board 260. The sealing section 270 includes a light-emitting-element sealing portion 271 for sealing the light emitting elements 221 and 222, a light-receiving-element sealing portion 272 for sealing the light receiving element 223, and a light shielding portion 273.

The light-emitting-element sealing portion 271 is formed from a translucent resin in a columnar shape of a generally elliptical arc in cross section and seals the light emitting elements 221 and 222. The light-emitting-element sealing portion 271 is exposed to a lateral surface 270a of the sealing section 270 on the side closer to the light emitting elements 221 and 222. The light-receiving-element sealing portion 272 is formed from a translucent resin in a columnar shape of a generally elliptical arc in cross section and seals the light receiving element 223. The light-receiving-element sealing portion 272 is exposed to a lateral surface 270b of the sealing section 270 on the side closer to the light receiving element 223. As the translucent resin forming the light-emitting-element sealing portion 271 and the light-receiving-element sealing portion 272, a transparent epoxy resin, for example, is used.

The light shielding portion 273 is formed by filling a resin having light-shielding properties into a region between the light-emitting-element sealing portion 271 and the light-receiving-element sealing portion 272 and into a peripheral region outside the light-emitting-element sealing portion 271 and the light-receiving-element sealing portion 272 on the principal surface 260a of the wiring board 260. The light shielding portion 273 defines two lateral surfaces 270c and 270d of the sealing section 270. As the light shielding portion 273, for example, an epoxy resin containing powder having light shielding properties, such as carbon black, is suitably used. The light shielding portion may be formed such that it surrounds all around the light-emitting-element sealing portion 271 and all around the light-receiving-element sealing portion 272 (see the above-described first embodiment).

The top surfaces of the above-described light-emitting-element sealing portion 271, light-receiving-element sealing portion 272, and light shielding portion 273 define a top surface 270e of the sealing section 270. The end region 251 of the base medium 250 on which the first electrocardiograph electrode 130 is disposed is bonded to the top surface 270e of the sealing section 270 with the adhesion layer 280 therebetween.

The first electrocardiograph electrode 230 is a plane electrode formed in the shape of a rectangular thin film, and is disposed in the end region 251 of the base medium 250. The first electrocardiograph electrode 230 is disposed between the light emitting elements 221 and 222 and the light receiving element 223 on the principal surface 250a of the base medium 250 when viewed from the direction 10 normal to the principal surface 260a of the wiring board 260. Moreover, the first electrocardiograph electrode 230 is disposed at a position at which it overlaps neither of the light emitting elements 221 and 222 nor the light receiving element 223 and at a position at which it overlaps neither of the opening 271a of the light-emitting-element sealing portion 271 nor the opening 272a of the light-receiving-element sealing portion 272 when viewed from the direction 10 normal to the principal surface 260a. The first and second electrocardiograph electrodes 130 and 140 are each constituted by a metallic thin film formed by, for example, plating, thin-film/thick-film process, or rolling.

As the adhesion layer 280, for example, double-sided tape without a core member, is suitably used. Alternatively, as the adhesion layer 280, double-sided tape including a translucent core member made from polyimide or PET and adhesive layers made from a translucent acrylic resin or the like and formed on both sides of the core member may be used.

The adhesion layer 280 is fully divided into two regions, one being closer to the light emitting elements 221 and 222 and the other being closer to the light receiving element 223. That is, the adhesion layer 280 is constituted by a first adhesion section 284 positioned closer to the light emitting elements 221 and 222, and a second adhesion section 285 positioned closer to the light receiving element 223.

The first and second adhesion sections 284 and 285 are each formed in a trapezoidal shape. As shown in FIG. 6, the first and second adhesion sections 284 and 285 are disposed with a spacing therebetween such that one trapezoid has an inverted shape of the other trapezoid (the top base and the bottom base are turned upside down). In FIG. 6, the hatched portion indicates the first and second adhesion sections 284 and 285.

A region between the first and second adhesion sections 284 and 285 will be referred to as a "division region 286". The direction in which a first division surface 284a of the first adhesion section 284 which faces the division region 286 extends is parallel with the direction in which a second division surface 285a of the second adhesion section 285 which faces the division region 286 extends. In this case, the direction in which the first and second division surfaces 284a and 285a extend will be referred to as a "division direction 14".

Figure 7:
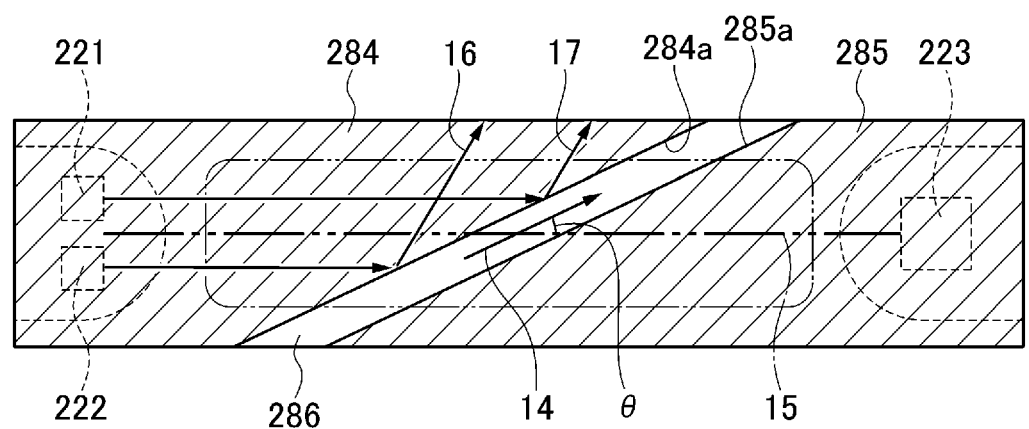
FIG. 7 is a view illustrating a propagation path of stray light in a divided adhesion layer.

A propagation path of stray light within the adhesion layer 280 will be described below with reference to FIG. 7. FIG. 7 is a view illustrating a propagation path of stray light in the divided adhesion layer 280. Normally, in the adhesion layer 280, stray light advancing in a direction from the light emitting elements 221 and 222 toward the light receiving element 223 is reflected or refracted at the division region 286.

In particular, for example, when the base medium 250 is formed from a resin and the division region 286 is air, if the division angle θ (details will be given later) is set to be 50° or smaller, as shown in FIG. 7, most of the amount of stray light propagating through the adhesion layer 280 deviates from a direction toward the light receiving element 223 at the division region 286. That is, for example, as in stray light 16 or 17, stray light is reflected on the boundary surface between the first adhesion section 284 and the division region 286.

Figure 8:
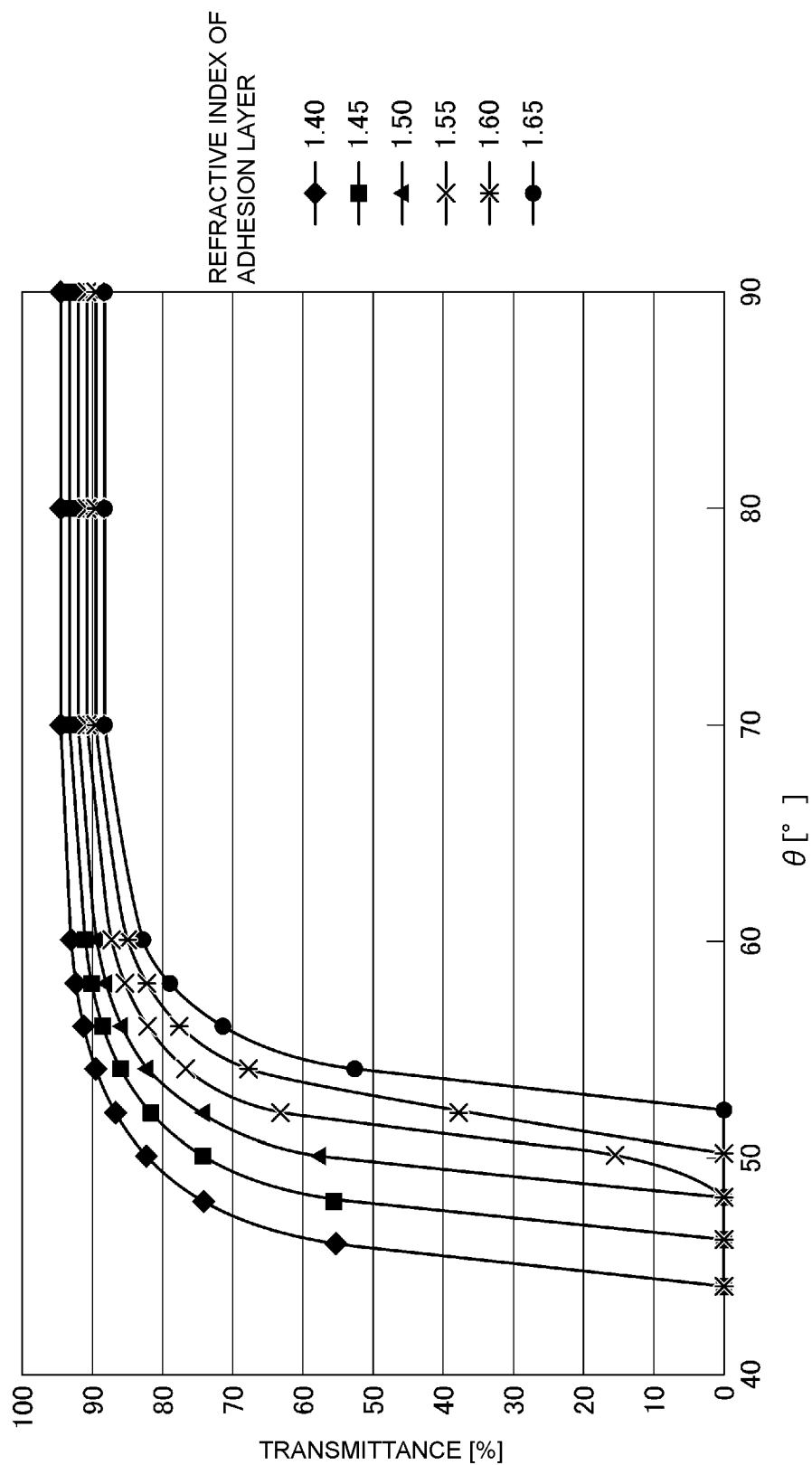
FIG. 8 is a graph illustrating the relationship between the division angle θ and the light transmittance.

The relationship between the transmittance and the angle (minor angle) θ between the division direction 14 and an imaginary straight line 15 (hereinafter such an angle will be referred to as the "division angle") is shown in FIG. 8. The imaginary straight line 15 is a straight line parallel with a straight line connecting the light emitting elements 221 and 222 and the light receiving element 223 in a plane parallel with the principal surface 260a of the wiring board 260. In this embodiment, since there are two light emitting elements, the imaginary straight line 15 is a straight line parallel with a direction 11 in which the intermediate point between the light emitting elements 221 and 222 is connected to the light receiving element 223.

In FIG. 8, the horizontal axis indicates the division angle θ, and the vertical axis indicates the transmittance. FIG. 8 shows the transmittance percentages of the adhesion layers 280 (double-sided tape) having a refractive index of 1.40, 1.45, 1.50, 1.55, 1.60, and 1.65 with respect to the division angle θ. FIG. 8 shows that as the transmittance is lower, the amount of stray light received through the adhesion layer 280 is smaller.

FIG. 8 shows that, when the division angle θ is 50° or smaller, the transmittance percentages of all the adhesion layers 280 having a refractive index of 1.40 through 1.65 are low. Accordingly, it is preferable that the division region 286 is formed such that the division angle θ is 50° or smaller.

When detecting biological information by using the biosensor 200, light emitted from the light emitting elements 221 and 222 passes through the light-emitting-element sealing portion 271 and impinges on the adhesion layer 280 through the opening 271a. Light then passes through the adhesion layer 280 and the base medium 250 and impinges on a fingertip. Light incident on and passing through the fingertip further passes through the base medium 250 and the adhesion layer 280 and impinges on the opening 272a of the light-receiving-element sealing portion 272. Then, light passes through the light-receiving-element sealing portion 272 and is received by the light receiving element 223. With this operation, a change in the intensity of light passing through the fingertip is obtained as a photoplethysmographic signal. At the same time, the potentials of fingertips (electrocardiogram) are obtained by the first and second electrocardiograph electrodes 230 and 240. That is, by using the biosensor 200, a photoplethysmographic signal and an electrocardiogram can be obtained simultaneously.

In the biosensor 200 of this embodiment, the light shielding portion 273 is disposed between the light-emitting-element sealing portion 271 and the light-receiving-element sealing portion 272. Accordingly, light emitted from the light emitting elements 221 and 222 is blocked from directly impinging on the light receiving element 223 by the provision of the light shielding portion 273. Meanwhile, part of light emitted from the light emitting elements 221 and 222 enters the adhesion layer 280 and the base medium 250 and propagates within the adhesion layer 280 and the base medium 250 toward the light receiving element 223. In this case, in the biosensor 200, the adhesion layer 280 is divided into a section positioned closer to the light emitting elements 221 and 222 and another section positioned closer to the light receiving element 223. Accordingly, stray light advancing in a direction from the light emitting elements 221 and 222 toward the light receiving element 223 in the adhesion layer 280 is reflected or refracted on the end surfaces 284a and 285a of the divided adhesion layers 284 and 285, respectively, thereby reducing the amount of stray light which enters the light receiving element 223 through the adhesion layer 280. Stray light propagating through the base medium 250 propagates until the second electrocardiograph electrode 240, and thus, it does not enter the light receiving element 223. As a result, in the biosensor 200 which simultaneously obtains a photoplethysmographic signal and the potentials of a body, it is possible to reduce the amount of stray light which is received without passing through a body (fingertip).

In this embodiment, since the adhesion layer 280 is divided such that the division angle θ is 50° or smaller, the reflectance of light reflected at the divided end surfaces 284a and 285a is increased. It is thus possible to further reduce the amount of stray light which is received through the adhesion layer 280.

In this embodiment, since the adhesion layer 280 is fully divided into a section positioned closer to the light emitting elements 221 and 222 and a section positioned closer to the light receiving element 223, the amount of reflected or refracted light is increased compared to a case in which the adhesion layer 280 is only partially divided. It is thus possible to further reduce the amount of stray light which does not pass through a body (fingertip) and which is received through the adhesion layer 280.

The biosensor 200 of the second embodiment has been discussed above. However, the present invention is not restricted to the above-described embodiment, and various modifications may be made. For example, in the above-described embodiment, the adhesion layer 280 is fully divided into the first and second adhesion sections 284 and 285. However, the present invention is not restricted to this configuration. It is sufficient that the adhesion layer 280 is at least partially divided into a section positioned closer to the light emitting elements 221 and 222 and a section positioned closer to the light receiving element 223. For example, the first and second adhesion sections 284 and 285 may be partially connected.

In the above-described embodiment, although the first and second adhesion sections 284 and 285 are formed in the same shape, they may be formed in different shapes. Additionally, it is not always necessary that the direction in which the first division surface 284a of the first adhesion section 284 extends be parallel with that in which the second division surface 285a of the second adhesion section 285 extends.

Moreover, the features of the biosensor 100 of the above-described first embodiment may be combined with the configuration of the biosensor 200. That is, the surface of the first electrocardiograph electrode 230 which is in contact with the base medium 250 may be roughened, and also, the refractive index of the base medium 250 may be set to be higher than that of the adhesion layer 280. This makes it easier for stray light to propagate through the base medium 250 having a higher refractive index. Stray light propagating through the base medium 250 is then scattered on the rough surface. Accordingly, it is possible to further reduce the amount of stray light which passes through the base medium 250 and the adhesion layer 280.

Alternatively, the top surface of the sealing section 270 may be roughened, and also, the refractive index of the adhesion layer 280 may be set to be higher than that of the base medium 250. This makes it easier for stray light to propagate through the adhesion layer 280 having a higher refractive index. Stray light propagating through the adhesion layer 280 is then scattered on the rough surface. Accordingly, it is possible to further reduce the amount of stray light which passes through the adhesion layer 280.

Although in the above-described embodiment double-sided tape is used as the adhesion layer 280, an adhesive, such as a resin, may be used. Moreover, in the above-described embodiment, two light emitting elements are provided. However, one light emitting element may be provided, or three or more light emitting elements may be provided. In the above-described embodiment, the first and second electrocardiograph electrodes 230 and 240 are disposed on one base medium 250. However, the first and second electrocardiograph electrodes 230 and 240 may be disposed on different base mediums.

In the above-described embodiment, a photoplethysmographic signal and an electrocardiogram are obtained simultaneously. However, if an electrocardiogram is not obtained, that is, only photoelectric pulse waves are measured, the provision of the first and second electrocardiograph electrodes 230 and 240 is not necessary, and thus, the first and second electrocardiograph electrodes 230 and 240 may be omitted.

(Third Embodiment)

Figure 9:
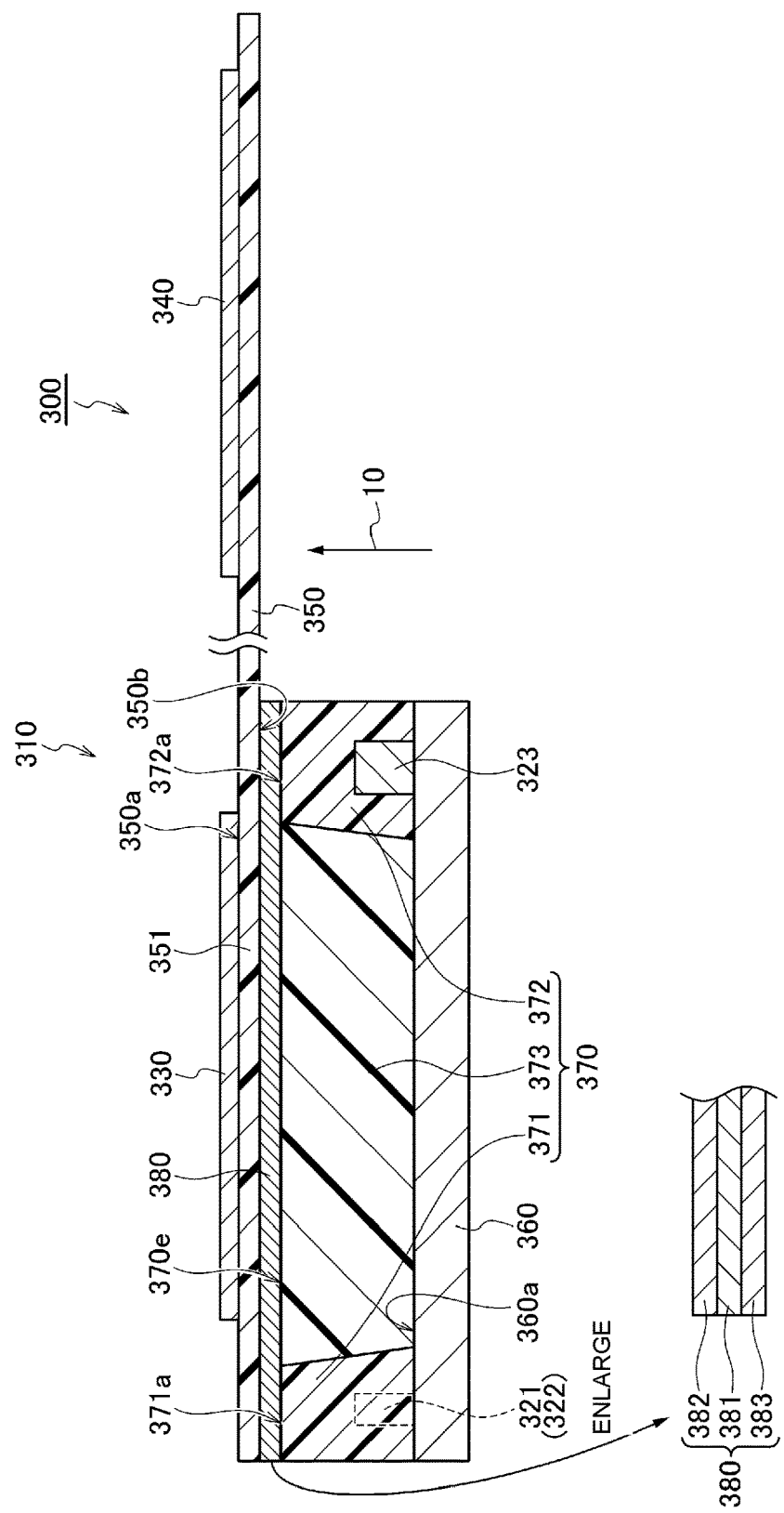
FIG. 9 is a longitudinal sectional view of a biosensor according to a third embodiment.
Figure 10:
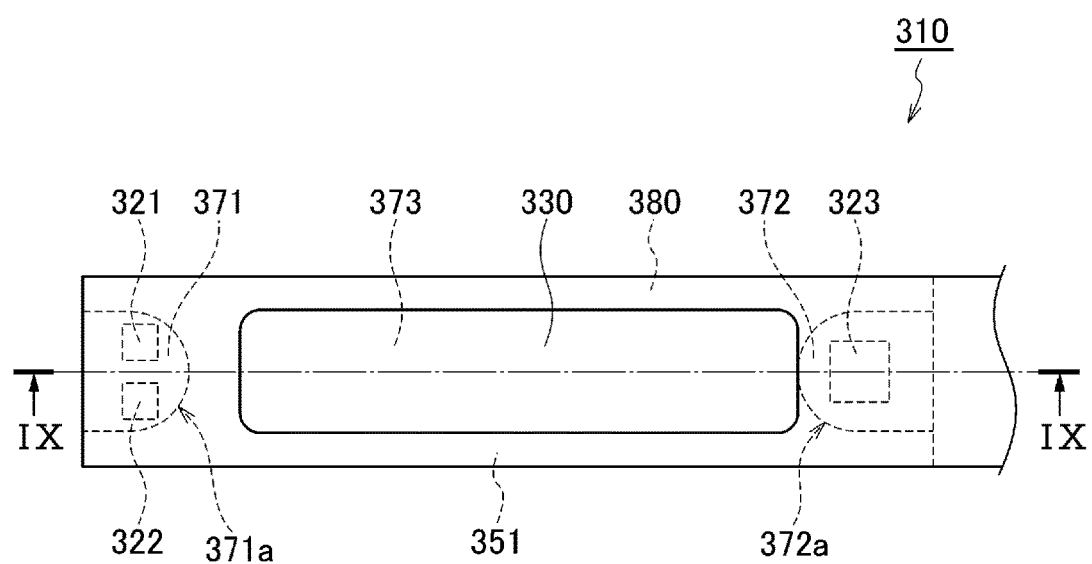
FIG. 10 is a plan view of a sensor unit forming the biosensor according to the third embodiment.

The configuration of a biosensor 300 according to a third embodiment will be described below with reference to FIGS. 9 and 10. An explanation of the configuration of the biosensor 300 identical to or similar to that of the biosensor 200 of the second embodiment will be omitted, and points different from those of the biosensor 200 will be principally described. FIG. 9 is a longitudinal sectional view of the biosensor 300. In FIG. 9, a sectional view taken along line IX-IX in FIG. 10 is shown. FIG. 10 is a plan view of a sensor unit 310 forming the biosensor 300.

The biosensor 300 includes two light emitting elements 321 and 322, a light receiving element 323, a first electrocardiograph electrode 330, a second electrocardiograph electrode 340, a base medium 350, a wiring board 360, a sealing section 370, and an adhesion layer 380. The light emitting elements 321 and 322, the light receiving element 323, the first electrocardiograph electrode 330, an end region 351 of the base medium 350, the wiring board 360, the sealing section 370, and the adhesion layer 380 are integrally formed. Hereinafter, for the sake of convenience, this integrally formed unit will be referred to as the "sensor unit 310".

The light transmitting properties of the adhesion layer 380 are more unique to this biosensor 300 than to the above-described biosensor 200. The adhesion layer 380 is not divided. The configurations of the other elements are similar to those of the biosensor 200, and thus, they will be simply explained. The light emitting elements 321 and 322 and the light receiving element 323 are mounted on a principal surface 360a of the wiring board 360. The sealing section 370 includes a light-emitting-element sealing portion 371, a light-receiving-element sealing portion 372, and a light shielding portion 373.

The light-emitting-element sealing portion 371 is formed from a translucent resin and seals the light emitting elements 321 and 322. The light-receiving-element sealing portion 372 is formed from a translucent resin and seals the light receiving element 323. The light shielding portion 373 is formed by filling a resin having light-shielding properties into a region between the light-emitting-element sealing portion 371 and the light-receiving-element sealing portion 372 and into a peripheral region outside the light-emitting-element sealing portion 371 and the light-receiving-element sealing portion 372. An opening 371a of the light-emitting-element sealing portion 371 and an opening 372a of the light-receiving-element sealing portion 372 are in contact with the adhesion layer 380.

The end region 351 of the base medium 350 on which the first electrocardiograph electrode 330 is disposed is bonded to a top surface 370e of the sealing section 370 with the adhesion layer 380 therebetween. The first electrocardiograph electrode 330 is disposed on a principal surface 350a of the base medium 350 such that it overlaps neither of the light emitting elements 321 and 322 nor the light receiving element 323 when viewed from the direction 10 normal to the principal surface 360a of the wiring board 360. The first electrocardiograph electrode 330 is also positioned between the light emitting elements 321 and 322 and the light receiving element 323 on the principal surface 350a of the base medium 350 when viewed from the direction 10 normal to the principal surface 360a.

The adhesion layer 380 has light transmitting properties, and the light transmittance of the adhesion layer 380 is set to be lower than that of the base medium 350. The adhesion layer 380 is constituted by double-sided tape including a core member 381 and adhesive layers 382 and 383 formed on both sides of the core member 381. The core member 381 is made of paper or nonwoven fabric. By forming the core member 381 of paper or nonwoven fabric, the transmittance of light propagating in the thickness direction or the longitudinal direction of the adhesion layer 380 can be set to be substantially lower than that of light propagating in the thickness direction or the longitudinal direction of the base medium 350. The adhesive layers 382 and 383 are made from, for example, an acrylic resin.

Since the core member 381 is thin, it relatively highly transmits light advancing in the thickness (vertical) direction of the core member 381. Accordingly, the adhesion layer 380 relatively sufficiently transmits light advancing upward from the light emitting elements 321 and 322 and light advancing downward toward the light receiving element 323. Thus, light emitted from the light emitting elements 321 and 322 advances upward through the adhesion layer 380 and impinges on a body. Light passing through the body advances downward through the adhesion layer 380 and impinges on the light receiving element 323. In contrast, stray light which propagates in the longitudinal direction of the adhesion layer 380 can be effectively reduced since the length of the adhesion layer 380 is long.

In the biosensor 300 according to this embodiment, when a fingertip contacts the front surface of the first electrocardiograph electrode 130, light emitted from the light emitting elements 321 and 322 impinges on the fingertip through the light-emitting-element sealing portion 371. Light passing through the fingertip is then received by the light receiving element 323 through the light-receiving-element sealing portion 372. With this operation, a photoplethysmographic signal indicating a pulse wave of the fingertip is obtained. At the same time, the potential of the fingertip which is in contact with the first electrocardiograph electrode 330 and the potential of the fingertip which is in contact with the second electrocardiograph electrode 340 are detected.

In the biosensor 300 according to this embodiment, the light transmittance of the adhesion layer 380 is set to be lower than that of the base medium 350. Accordingly, stray light entering the adhesion layer 380 attenuates more intently as it propagates through the adhesion layer 380 in a direction from the light emitting elements 321 and 322 toward the light receiving element 323, thereby reducing the amount of stray light which enters the light receiving element 323. Stray light propagating through the base medium 350 propagates until the second electrocardiograph electrode 340, and thus, it does not enter the light receiving element 323. As a result, in the biosensor which simultaneously obtains a photoplethysmographic signal and potentials of a body (electrocardiogram), it is possible to reduce the amount of stray light which is received without passing through a body.

In the biosensor 300 according to this embodiment, in particular, the core member 381 forming the adhesion layer 380 is made of paper or nonwoven fabric. This makes it relatively easy for light to pass in the thickness direction of the core member 381 and relatively difficult for light to pass in the longitudinal direction of the core member 381. Thus, it is possible to allow light which is emitted from the light emitting elements 321 and 322 and which will impinge on a body and light which has passed through the body and which will impinge on the light receiving element 323 to pass through the core member 381, and to reduce stray light propagating through the core member 381 in a direction from the light emitting elements 321 and 322 to the light receiving element 323.

The third embodiment has been discussed above. However, the present invention is not restricted to the above-described embodiment, and various modifications may be made. For example, in the above-described embodiment, double-sided tape is used as the adhesion layer 380. However, an adhesive, such as a resin having an adjusted light transmittance ratio, may be used.

Moreover, the features of the biosensor 100 of the above-described first embodiment may be combined with the configuration of the biosensor 300. That is, the surface of the first electrocardiograph electrode 330 which is in contact with the base medium 350 may be roughened, and also, the refractive index of the base medium 350 may be set to be higher than that of the adhesion layer 380. This makes it easier for stray light to propagate through the base medium 350 having a higher refractive index. Stray light propagating through the base medium 350 is then scattered on the rough surface. Accordingly, it is possible to further reduce the amount of stray light which passes through the base medium 350 and the adhesion layer 380. Alternatively, the top surface of the sealing section 370 may be roughened, and also, the refractive index of the adhesion layer 380 may be set to be higher than that of the base medium 350. In this case, too, it is possible to further reduce the amount of stray light which passes through the base medium 350 and the adhesion layer 380.

Moreover, the features of the biosensor 200 of the above-described second embodiment may be combined with the configuration of the biosensor 300. That is, the adhesion layer 380 may be divided into a section closer to the light emitting elements 321 and 322 and a section closer to the light receiving element 323. In this case, part of stray light propagating through the adhesion layer 380 in a direction from the light emitting elements 321 and 322 to the light receiving element 323 is reflected or refracted at the divided portion. It is thus possible to further reduce the amount of stray light which does not pass through a body and which is received through the adhesion layer 380. In this case, if the adhesion layer 380 is divided in a direction such that the division angle θ is set to be 50° or smaller, the reflectance of light reflected at the divided portion is increased, thereby making it possible to reduce stray light more effectively.

In this embodiment, a photoplethysmographic signal and an electrocardiogram are obtained simultaneously. However, if an electrocardiogram is not obtained, that is, only photoelectric pulse waves are measured, the provision of the first and second electrocardiograph electrodes 330 and 340 is not necessary, and thus, the first and second electrocardiograph electrodes 330 and 340 may be omitted.

(Fourth Embodiment)

Figure 11:
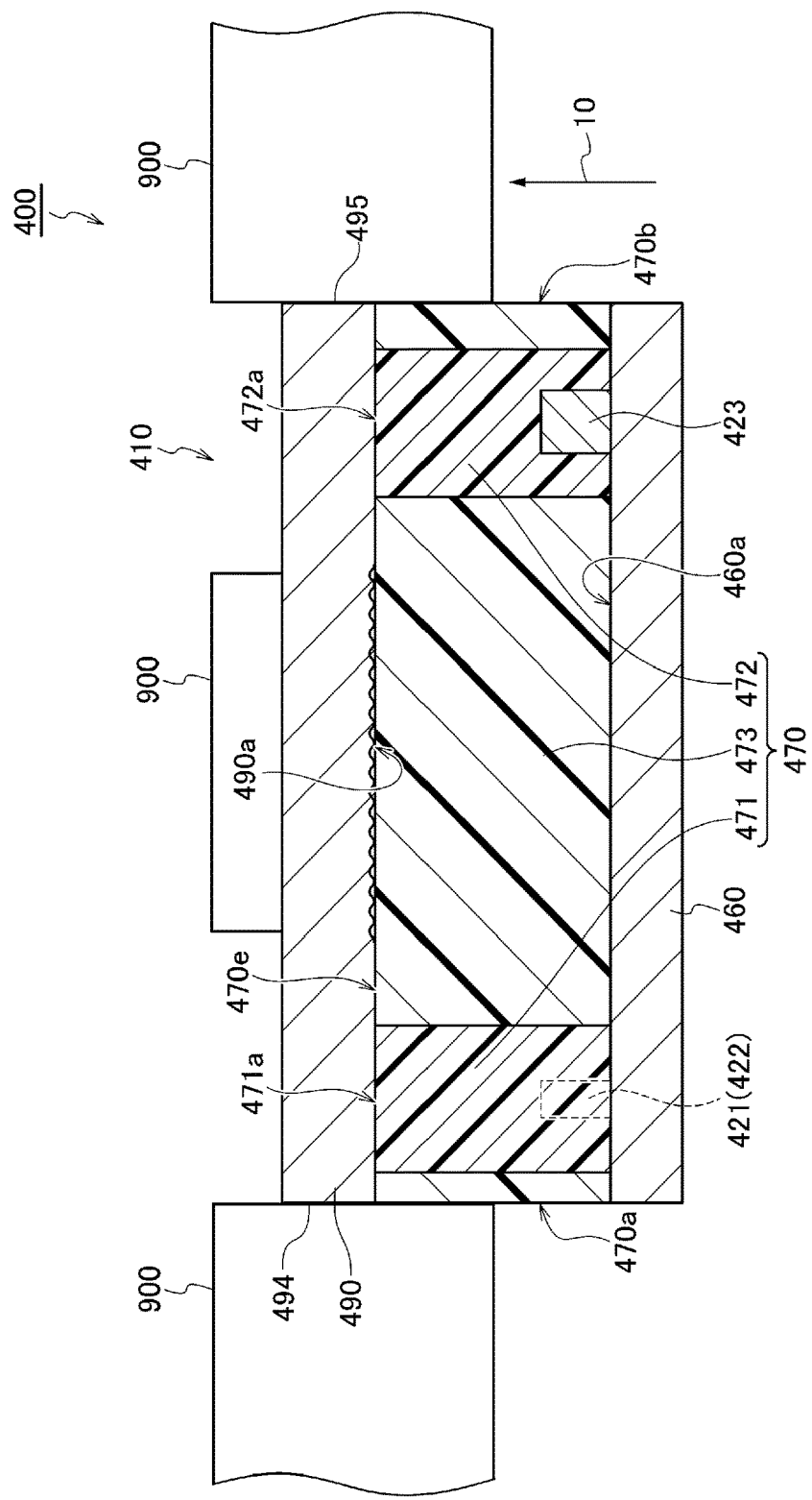
FIG. 11 is a longitudinal sectional view of a biosensor according to a fourth embodiment.
Figure 12:
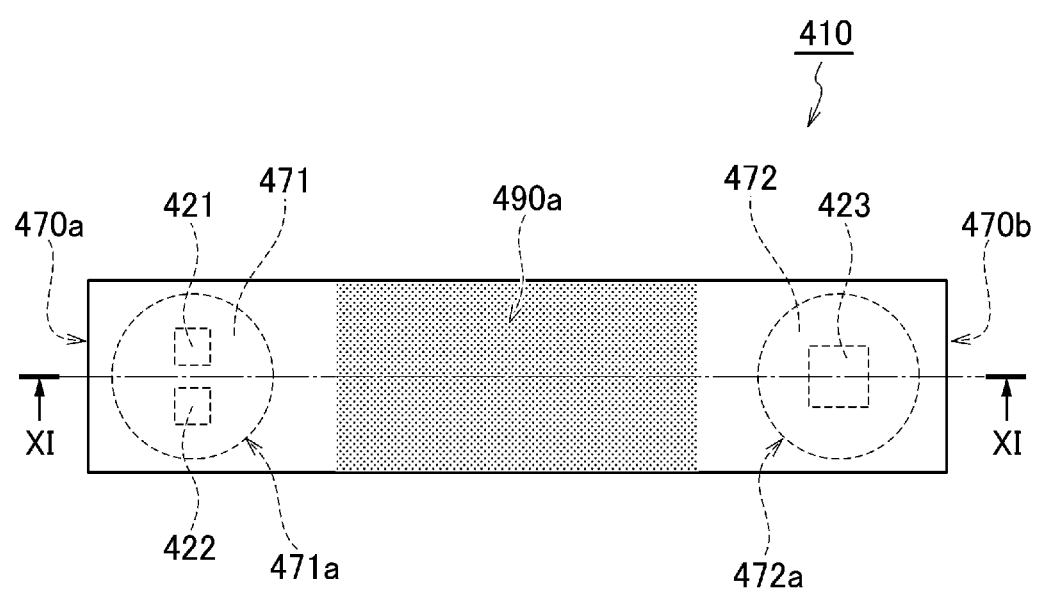
FIG. 12 is a plan view of a sensor unit forming the biosensor according to the fourth embodiment.

The configuration of a biosensor 400 according to a fourth embodiment will be described below with reference to FIGS. 11 and 12. FIG. 11 is a longitudinal sectional view of the biosensor 400. In FIG. 11, a sectional view taken along line XI-XI in FIG. 12 is shown. FIG. 12 is a plan view of a sensor unit 410 forming the biosensor 400.

The biosensor 400 is a sensor which performs detection (monitoring) of biological information, for example, measuring of the pulse and oxygen saturation, upon a fingertip touching the biosensor 400. The biosensor 400 optically measures the pulse and oxygen saturation by utilizing absorption characteristics of hemoglobin within the blood.

In order to implement this function, the biosensor 400 includes two light emitting elements 421 and 422, a light receiving element 423, a wiring board 460, a sealing section 470, and a cover 490.

The wiring board 460 is formed in a rectangular sheet-like shape. On the wiring board 460, the light emitting elements 421 and 422, the light receiving element 423, the sealing section 470, and the cover 490 are integrally formed. Hereinafter, for the sake of convenience, this integrally formed unit will be referred to as the "sensor unit 410". This sensor unit 410 is formed generally in a rectangular parallelepiped. In FIG. 11, the height is shown in a relatively enlarged dimension for representation. The sensor unit 410 is attached to a casing 900 which is made from an opaque resin by means of, for example, the insertion of the sensor unit 410 into a rectangular hole formed in the casing 900.

The light emitting elements 421 and 422 and the light receiving element 423 are mounted on a principal surface 460a of the wiring board 460 formed in a rectangular shape. The light emitting elements 421 and 422 are disposed side by side on a shorter side of the wiring board 460 at one end portion of the principal surface 460a. Meanwhile, the light receiving element 423 is disposed at the other end portion of the principal surface 460a. The distance from the light emitting elements 421 and 422 to the light receiving element 423 is set to be, for example, about 4 to 20 mm.

The two light emitting elements 421 and 422 emit light beams of different wavelengths in order to obtain the ratio of oxyhemoglobin to deoxyhemoglobin indicating oxygen saturation within the blood. For example, the light emitting element 421 emits light around an infrared light range in which the absorption coefficient of oxyhemoglobin is high. The light emitting element 422 emits light around a red light range in which the absorption coefficient of deoxyhemoglobin is high.

As the light emitting elements 421 and 422, LED, VCSEL (Vertical Cavity Surface Emitting LASER), a resonator LED, or the like, may be used. As the light receiving element 423, a photodiode, a phototransistor, or the like, may be suitably used.

The sealing section 470 is formed in the shape of a rectangular parallelepiped on the principal surface 460a of the wiring board 460. The sealing section 470 includes a light-emitting-element sealing portion 471 for sealing the light emitting elements 421 and 422, a light-receiving-element sealing portion 472 for sealing the light receiving element 423, and a light shielding portion 473.

The light-emitting-element sealing portion 471 is formed from a translucent resin in a cylindrical shape and seals the light emitting elements 421 and 422. The light-receiving-element sealing portion 472 is formed from a translucent resin in a cylindrical shape and seals the light receiving element 423. As the translucent resin forming the light-emitting-element sealing portion 471 and the light-receiving-element sealing portion 472, a transparent epoxy resin, for example, is used.

The light shielding portion 473 is formed by filling a resin having light-shielding properties into a region between the light-emitting-element sealing portion 471 and the light-receiving-element sealing portion 472 and into a region around the light-emitting-element sealing portion 471 and the light-receiving-element sealing portion 472 on the principal surface 460*a* of the wiring board 460. The light shielding portion 473 defines four lateral surfaces of the sealing section 470. As the light shielding portion 473, for example, an epoxy resin containing powder having light shielding properties, such as carbon black, is suitably used.

The top surfaces of the above-described light-emitting-element sealing portion 471, light-receiving-element sealing portion 472, and light shielding portion 473 define a top surface 470*e* of the sealing section 470. The cover 490 having light transmitting properties is attached to the top surface 470*e* of the sealing section 470. The cover 490 has the same shape and the same size as the top surface 470*e* of the sealing section 470, and overlaps the top surface 470*e* of the sealing section 470. That is, the cover 490 covers an opening 471*a* of the light-emitting-element sealing portion 471 and an opening 472*a* of the light-receiving-element sealing portion 472.

An end portion 494 of the cover 490 closer to the light emitting elements 421 and 422 is positioned farther outward (toward a lateral surface 470*a*) than the opening 471*a* of the light-emitting-element sealing portion 471. That is, the end portion 494 of the cover 490 is disposed such that it does not overlap the opening 471*a* when viewed from the direction 10 normal to the principal surface 460*a* of the wiring board 460.

An end portion 495 of the cover 490 closer to the light receiving element 423 is positioned farther outward (toward a lateral surface 470*b*) than the opening 472*a* of the light-receiving-element sealing portion 472. That is, the end portion 495 of the cover 490 is disposed such that it does not overlap the opening 472*a* when viewed from the direction 10 normal to the principal surface 460*a*.

The cover 490 is made from an acrylic, polycarbonate, or PET (polyethylene terephthalate) resin having translucent properties. A central portion of a surface (bottom surface) of the cover 490 which is in contact with the sealing section 470 (a region which overlaps neither of the opening 471*a* of the light-emitting-element sealing portion 471 nor the opening 472*a* of the light-receiving-element sealing portion 472 when viewed from the direction 10 normal to the principal surface 460*a* of the wiring board 460 (see FIG. 12)) is roughened so that light (stray light) propagating through the cover 490 can be scattered. It is preferable that the cover 490 is formed in a sheet-like shape having a thickness of about 0.1 to 2 mm and that the surface roughness of the cover 490 is comparable to or higher than a polishing surface of #100 or smaller. That is, the arithmetic average of the roughness profile Ra is several micrometers (µm) or smaller (more preferably, one micrometer or smaller). Hereinafter, the region of the cover 490 which is roughened will be referred to as a "rough surface 490*a*".

The detection of biological information by using the biosensor 400 is performed by allowing a part of a body, for example, a fingertip of a left hand of a patient, to contact the biosensor 400. When detecting biological information, light emitted from the light emitting elements 421 and 422 passes through the light-emitting-element sealing portion 471 and impinges on the cover 490 through the opening 471*a*. Light then passes through the cover 490 and impinges on the fingertip.

Light incident on and passing through the fingertip further passes through the cover 490 and impinges on the opening 472*a* of the light-receiving-element sealing portion 472. Then, light passes through the light-receiving-element sealing portion 472 and is received by the light receiving element 423. With this operation, a change in the intensity of light passing through the fingertip is obtained as a photoplethysmographic signal. In this case, since light beams of different wavelengths are emitted from the two light emitting elements 421 and 422, the intensity of the transmitted light concerning the two wavelengths can be obtained.

The cover 490 having light transmitting properties is disposed between the light emitting elements 421 and 422 and the fingertip 12. Accordingly, part of light emitted from the light emitting elements 421 and 422 propagates through the cover 490 toward the light receiving element 423. In this biosensor 400, the back surface 490*a* of the cover 490 is roughened so that light passing through the cover 490 may be scattered. Accordingly, light (stray light) entering the cover 490 is scattered in the rough region of the back surface 490*a* when advancing within the cover 490 while being reflected. Accordingly, the amount of stray light which enters the light receiving element 423 is reduced.

As discussed above in detail, in the biosensor 400 according to this embodiment, when a fingertip contacts the front surface of the biosensor 400, light emitted from the light emitting elements 421 and 422 impinges on the fingertip via the light-emitting-element sealing portion 471 and the cover 490. Then, light passing through the fingertip is received by the light receiving element 423 via the cover 490 and the light-receiving-element sealing portion 472. With this operation, a photoplethysmographic signal indicating a pulse wave of the fingertip 12 is obtained.

In the biosensor 400, the light shielding portion 473 is disposed between the light-emitting-element sealing portion 471 and the light-receiving-element sealing portion 472. Accordingly, light emitted from the light emitting elements 421 and 422 is blocked from directly impinging on the light receiving element 423 by the provision of the light shielding portion 473. Meanwhile, light entered the cover 490 advances within the cover 490 while being reflected. In this case, since the back surface 490*a* of the cover 490 is roughened, stray light which advances within the cover 490 is scattered by the formation of the rough back surface 490*a*, thereby reducing the amount of stray light which enters the light receiving element 423. As a result, in the biosensor 400 which obtains a photoplethysmographic signal, it is possible to reduce the amount of stray light which is received without passing through the fingertip 12.

In this embodiment, the back surface (bottom surface) of the cover 490 is roughened. Alternatively, instead of or in addition to the back surface of the cover 490, the top surface of the cover 490 may be roughened.

(Fifth Embodiment)

Figure 13:
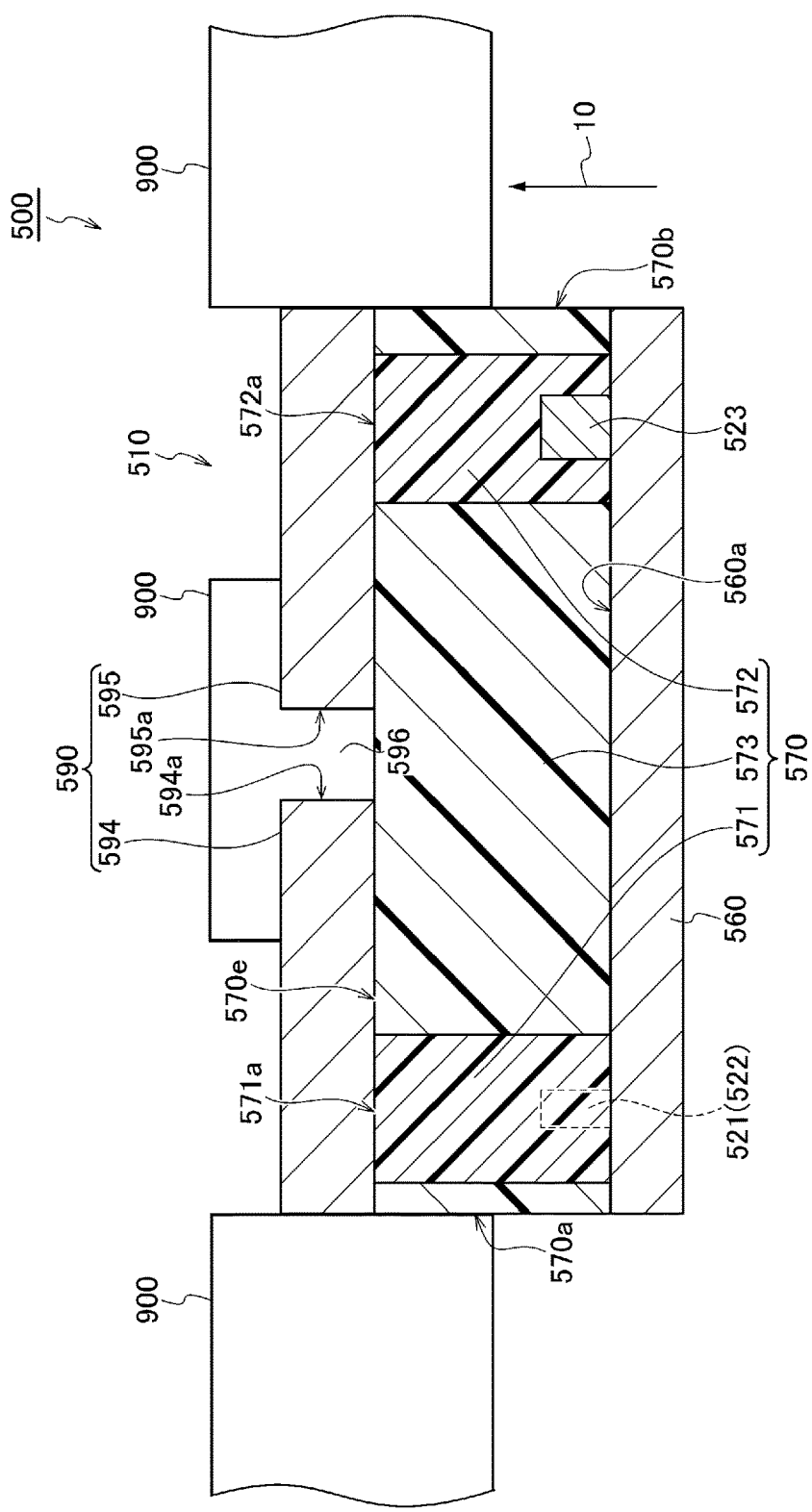
FIG. 13 is a longitudinal sectional view of a biosensor according to a fifth embodiment.
Figure 14:
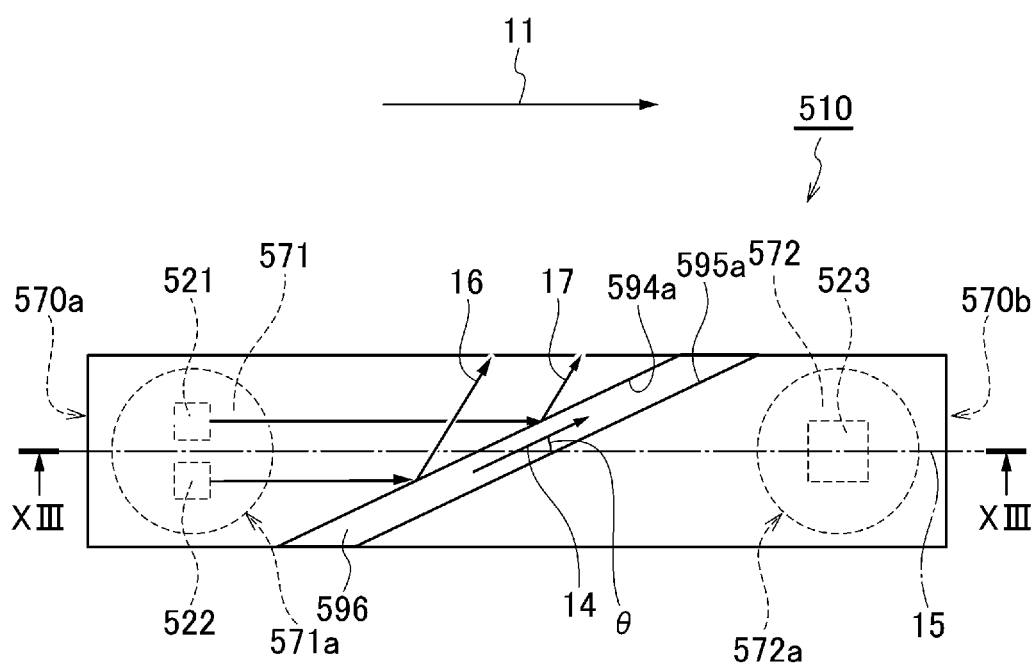
FIG. 14 is a plan view of a sensor unit forming the biosensor according to the fifth embodiment.

The configuration of a biosensor 500 according to a fifth embodiment will be described below with reference to FIGS. 13 and 14. Only a simple explanation will be given of the configuration of the biosensor 500 identical to or similar to that of the biosensor 400 of the above-described fourth embodiment, and points different from those of the biosensor 400 will be principally described. FIG. 13 is a longitudinal sectional view of the biosensor 500. In FIG. 13, a sectional view taken along line XIII-XIII in FIG. 14 is shown. FIG. 14 is a plan view of a sensor unit 510 forming the biosensor 500.

The biosensor 500 is a sensor which performs detection (monitoring) of biological information, for example, measuring of the pulse and oxygen saturation, upon a fingertip touching the biosensor 500. The biosensor 500 optically measures the pulse and oxygen saturation by utilizing absorption characteristics of hemoglobin within the blood.

In order to implement this function, the biosensor 500 includes two light emitting elements 521 and 522, a light receiving element 523, a wiring board 560, a sealing section 570, and a cover 590.

The wiring board 560 is formed in a rectangular sheet-like shape. On the wiring board 560, the light emitting elements 521 and 522, the light receiving element 523, the sealing section 570, and the cover 590 are integrally formed. Hereinafter, for the sake of convenience, this integrally formed unit will be referred to as the "sensor unit 510". This sensor unit 510 is formed generally in a rectangular parallelepiped. In FIG. 13, the height is shown in a relatively enlarged dimension for representation. The sensor unit 510 is attached to a casing 900 which is made from an opaque resin by means of, for example, the insertion of the sensor unit 510 into a rectangular hole formed in the casing 900.

The light emitting elements 521 and 522 and the light receiving element 523 are mounted on a principal surface 560a of the wiring board 560 formed in a rectangular shape. The light emitting elements 521 and 522 are disposed side by side on a shorter side of the wiring board 560 at one end portion of the principal surface 560a. Meanwhile, the light receiving element 523 is disposed at the other end portion of the principal surface 560a. The distance from the light emitting elements 521 and 522 to the light receiving element 523 is set to be, for example, about 4 to 20 mm.

The two light emitting elements 521 and 522 emit light beams of different wavelengths in order to obtain the ratio of oxyhemoglobin to deoxyhemoglobin indicating oxygen saturation within the blood. For example, the light emitting element 521 emits light around an infrared light range in which the absorption coefficient of oxyhemoglobin is high. The light emitting element 522 emits light around a red light range in which the absorption coefficient of deoxyhemoglobin is high.

As the light emitting elements 521 and 522, LED, VCSEL, a resonator LED, or the like, may be used. As the light receiving element 523, a photodiode, a phototransistor, or the like, may be suitably used.

The sealing section 570 is formed in the shape of a rectangular parallelepiped on the principal surface 560a of the wiring board 560. The sealing section 570 includes a light-emitting-element sealing portion 571 for sealing the light emitting elements 521 and 522, a light-receiving-element sealing portion 572 for sealing the light receiving element 523, and a light shielding portion 573.

The light-emitting-element sealing portion 571 is formed from a translucent resin in a cylindrical shape and seals the light emitting elements 521 and 522. The light-receiving-element sealing portion 572 is formed from a translucent resin in a cylindrical shape and seals the light receiving element 523. As the translucent resin forming the light-emitting-element sealing portion 571 and the light-receiving-element sealing portion 572, a transparent epoxy resin, for example, is used.

The light shielding portion 573 is formed by filling a resin having light-shielding properties into a region between the light-emitting-element sealing portion 571 and the light-receiving-element sealing portion 572 and into a region around the light-emitting-element sealing portion 571 and the light-receiving-element sealing portion 572 on the principal surface 560a of the wiring board 560. The light shielding portion 573 defines four lateral surfaces of the sealing section 570. As the light shielding portion 573, for example, an epoxy resin containing powder having light shielding properties, such as carbon black, is suitably used.

The top surfaces of the above-described light-emitting-element sealing portion 571, light-receiving-element sealing portion 572, and light shielding portion 573 define a top surface 570e of the sealing section 570. The cover 590 having light transmitting properties is attached to the top surface 570e of the sealing section 570.

The cover 590 is fully divided into two regions, one being closer to the light emitting elements 521 and 522 and the other being closer to the light receiving element 523. That is, the cover 590 is constituted by a first cover member 594 positioned closer to the light emitting elements 521 and 522, and a second cover member 595 positioned closer to the light receiving element 523. The first and second cover members 594 and 595 are each made from an acrylic, polycarbonate, or PET (polyethylene terephthalate) resin.

The first and second cover members 594 and 595 are each formed in a trapezoidal shape. As shown in FIG. 14, the first and second cover members 594 and 595 are disposed with a spacing therebetween such that one trapezoid has an inverted shape of the other trapezoid (the top base and the bottom base are turned upside down).

A region between the first and second cover members 594 and 595 is referred to as a "division region 596". The direction in which a first division surface 594a of the first cover member 594 which faces the division region 596 extends is parallel with the direction in which a second division surface 595a of the second cover member 595 which faces the division region 596 extends. In this case, the direction in which the first and second division surfaces 594a and 595a extend will be referred to as a "division direction 14".

Normally, in the cover 590, stray light advancing in a direction from the light emitting elements 521 and 522 toward the light receiving element 523 is reflected or refracted at the division region 596. In particular, if the division angle θ is set to be 50° or smaller, as shown in FIG. 14, most of the amount of stray light propagating through the cover 590 deviates from a direction toward the light receiving element 523 at the division region 596. That is, for example, as in stray light 16 or 17, stray light is reflected on the boundary surface between the first cover member 594 and the division region 596.

It is thus preferable that the division region 596 is formed such that the angle (minor angle) θ between the division direction 14 and an imaginary straight line 15 (division angle) is 50° or smaller. The imaginary straight line 15 is a straight line parallel with a straight line connecting the light emitting elements 521 and 522 and the light receiving element 523 in a plane parallel with the principal surface 560a of the wiring board 560. In this embodiment, since there are two light emitting elements, the imaginary straight line 15 is a straight line parallel with a direction 11 in which the intermediate point between the light emitting elements 521 and 522 is connected to the light receiving element 523.

When detecting biological information by using the biosensor 500, light emitted from the light emitting elements 521 and 522 passes through the light-emitting-element sealing portion 571 and impinges on the cover 590 through the opening 571a. Light then passes through the cover 590 and impinges on a fingertip. Light incident on and passing through the fingertip further passes through the cover 590 and impinges on the opening 572a of the light-receiving-element sealing portion 572. Then, light passes through the light-receiving-element sealing portion 572 and is received by the light receiving element 523. With this operation, a change in the intensity of light passing through the fingertip is obtained as a photoplethysmographic signal.

In the biosensor 500 of this embodiment, the light shielding portion 573 is disposed between the light-emitting-element sealing portion 571 and the light-receiving-element sealing portion 572. Accordingly, light emitted from the light emitting elements 521 and 522 is blocked from directly impinging on the light receiving element 523 by the provision of the light shielding portion 573. Meanwhile, part of light emitted from the light emitting elements 521 and 522 propagates through the cover 590. In this case, in the biosensor 500, the cover 590 is divided into a member positioned closer to the light emitting elements 521 and 522 and another member positioned closer to the light receiving element 523. Accordingly, stray light advancing in a direction from the light emitting elements 521 and 522 toward the light receiving element 523 in the cover 590 is reflected or refracted on the end surfaces 594a and 595a of the divided first and second cover members 594 and 595, respectively, thereby reducing the amount of stray light which enters the light receiving element 523 through the cover 590. As a result, in the biosensor 500 which obtains a photoplethysmographic signal, it is possible to reduce the amount of stray light which is received without passing through a body (fingertip).

In this embodiment, since the cover 590 is divided such that the division angle θ is 50° or smaller, the reflectance of light reflected at the divided end surfaces 594a and 595a is increased. It is thus possible to further reduce the amount of stray light which is received through the cover 590.

In this embodiment, since the cover 590 is fully divided into a member positioned closer to the light emitting elements 521 and 522 and a member positioned closer to the light receiving element 523, the amount of reflected or refracted light is increased compared to a case in which the cover 590 is only partially divided. It is thus possible to further reduce the amount of stray light which does not pass through a body (fingertip) and which is received through the cover 590.

The biosensor 500 according to the fifth embodiment has been discussed above. However, the present invention is not restricted to the above-described embodiment, and various modifications may be made. For example, in the above-described embodiment, the cover 590 is fully divided into the first and second cover members 594 and 595. However, the present invention is not restricted to this configuration. It is sufficient that the cover 590 is at least partially divided into a member positioned closer to the light emitting elements 521 and 522 and a member positioned closer to the light receiving element 523. For example, the first and second cover members 594 and 595 may be partially connected.

In the above-described embodiment, although the first and second cover members 594 and 595 are formed in the same shape, they may be formed in different shapes. Additionally, it is not always necessary that the direction in which the first division surface 594a of the first cover member 594 extends be parallel with that in which the second division surface 595a of the second cover member 595 extends. Moreover, in the embodiment shown in FIG. 13, the casing 900 is embedded in the division region 596. However, the casing 900 does not have to be embedded in the division region 596.

(Sixth Embodiment)

Figure 15:
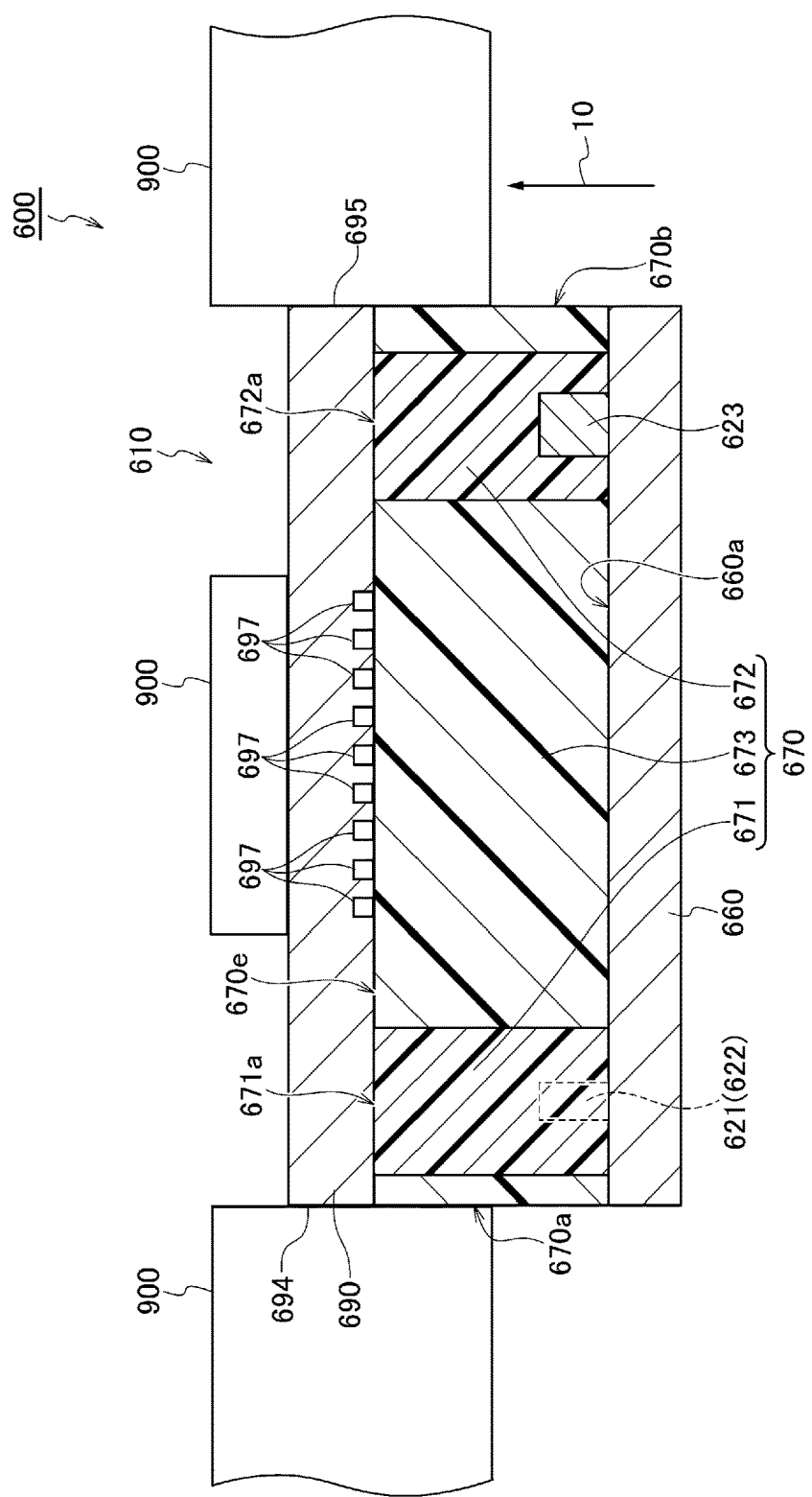
FIG. 15 is a longitudinal sectional view of a biosensor according to a sixth embodiment.
Figure 16:
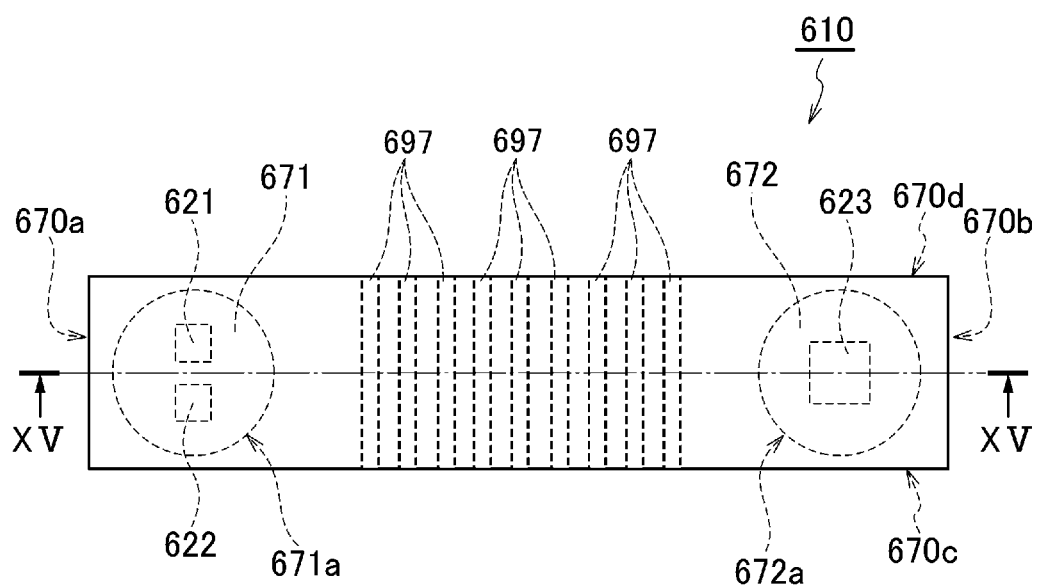
FIG. 16 is a plan view of a sensor unit forming the biosensor according to the sixth embodiment.
Figure 17:
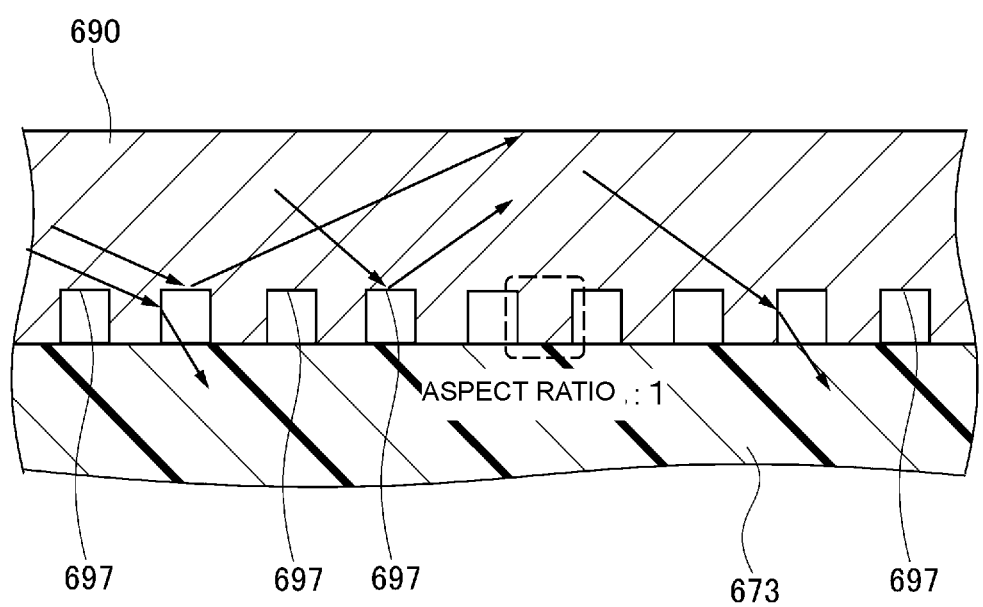
FIG. 17 is a view illustrating a propagation path of stray light at grooves formed in a cover.

The configuration of a biosensor 600 according to a sixth embodiment will be described below with reference to FIGS. 15 through 17. Only a simple explanation will be given of the configuration of the biosensor 600 identical to or similar to that of the biosensor 400 of the above-described fourth embodiment, and points different from those of the biosensor 400 will be principally described. FIG. 15 is a longitudinal sectional view of the biosensor 600. In FIG. 15, a sectional view taken along line XV-XV in FIG. 16 is shown. FIG. 16 is a plan view of a sensor unit 610 forming the biosensor 600. FIG. 17 is a view illustrating a propagation path of stray light at grooves 697 formed in a cover 690.

The biosensor 600 is a sensor which performs detection (monitoring) of biological information, for example, measuring of the pulse and oxygen saturation, upon a fingertip touching the biosensor 600. The biosensor 600 optically measures the pulse and oxygen saturation by utilizing absorption characteristics of hemoglobin within the blood.

In order to implement this function, the biosensor 600 includes two light emitting elements 621 and 622, a light receiving element 623, a wiring board 660, a sealing section 670, and a cover 690.

The wiring board 660 is formed in a rectangular sheet-like shape. On the wiring board 660, the light emitting elements 621 and 622, the light receiving element 623, the sealing section 670, and the cover 690 are integrally formed. Hereinafter, for the sake of convenience, this integrally formed unit will be referred to as the "sensor unit 610". This sensor unit 610 is formed generally in a rectangular parallelepiped. In FIG. 15, the height is shown in a relatively enlarged dimension for representation. The sensor unit 610 is attached to a casing 900 which is made from an opaque resin by means of, for example, the insertion of the sensor unit 610 into a rectangular hole formed in the casing 900.

The light emitting elements 621 and 622 and the light receiving element 623 are mounted on a principal surface 660a of the wiring board 660 formed in a rectangular shape. The light emitting elements 621 and 622 are disposed side by side on a shorter side of the wiring board 660 at one end portion of the principal surface 660a. Meanwhile, the light receiving element 623 is disposed at the other end portion of the principal surface 660a. The distance from the light emitting elements 621 and 622 to the light receiving element 623 is set to be, for example, about 4 to 20 mm.

The two light emitting elements 621 and 622 emit light beams of different wavelengths in order to obtain the ratio of oxyhemoglobin to deoxyhemoglobin indicating oxygen saturation within the blood. For example, the light emitting element 621 emits light around an infrared light range in which the absorption coefficient of oxyhemoglobin is high. The light emitting element 622 emits light around a red light range in which the absorption coefficient of deoxyhemoglobin is high.

As the light emitting elements 621 and 622, LED, VCSEL (Vertical Cavity Surface Emitting LASER), a resonator LED, or the like, may be used. As the light receiving element 623, a photodiode, a phototransistor, or the like, may be suitably used.

The sealing section 670 is formed in the shape of a rectangular parallelepiped on the principal surface 660a of the wiring board 660. The sealing section 670 includes a light-emitting-element sealing portion 671 for sealing the light emitting elements 621 and 622, a light-receiving-element sealing portion 672 for sealing the light receiving element 623, and a light shielding portion 673.

The light-emitting-element sealing portion 671 is formed from a translucent resin in a cylindrical shape and seals the light emitting elements 621 and 622. The light-receiving-element sealing portion 672 is formed from a translucent resin in a cylindrical shape and seals the light receiving element 623. As the translucent resin forming the light-emitting-element sealing portion 671 and the light-receiving-element sealing portion 672, a transparent epoxy resin, for example, is used.

The light shielding portion 673 is formed by filling a resin having light-shielding properties into a region between the light-emitting-element sealing portion 671 and the light-receiving-element sealing portion 672 and into a region around the light-emitting-element sealing portion 671 and the light-receiving-element sealing portion 672 on the principal surface 660a of the wiring board 660. The light shielding portion 673 defines four lateral surfaces of the sealing section 670. As the light shielding portion 673, for example, an epoxy resin containing powder having light shielding properties, such as carbon black, is suitably used.

The top surfaces of the above-described light-emitting-element sealing portion 671, light-receiving-element sealing portion 672, and light shielding portion 673 define a top surface 670e of the sealing section 670. The cover 690 having light transmitting properties is attached to the top surface 670e of the sealing section 670. The cover 690 has the same shape and the same size as the top surface 670e of the sealing section 670, and overlaps the top surface 670e of the sealing section 670. That is, the cover 690 covers an opening 671a of the light-emitting-element sealing portion 671 and an opening 672a of the light-receiving-element sealing portion 672.

An end portion 694 of the cover 690 closer to the light emitting elements 621 and 622 is positioned farther outward (toward a lateral surface 670a) than the opening 671a of the light-emitting-element sealing portion 671. That is, the end portion 694 of the cover 690 is disposed such that it does not overlap the opening 671a when viewed from the direction 10 normal to the principal surface 660a of the wiring board 660.

An end portion 695 of the cover 690 closer to the light receiving element 623 is positioned farther outward (toward a lateral surface 670b) than the opening 672a of the light-receiving-element sealing portion 672. That is, the end portion 695 of the cover 690 is disposed such that it does not overlap the opening 672a when viewed from the direction 10 normal to the principal surface 660a.

The cover 690 is made from polyimide or PET (polyethylene terephthalate) having light transmitting properties. In a central portion of a surface (bottom surface) of the cover 690 which is in contact with the sealing section 670 (a region which overlaps neither of the opening 671a of the light-emitting-element sealing portion 671 nor the opening 672a of the light-receiving-element sealing portion 672 when viewed from the direction 10 normal to the principal surface 660a of the wiring board 660 (see FIG. 16)), a plurality of grooves (recessed portions) 697 are formed. The plurality of grooves 697 are formed in a direction intersecting with (in this embodiment, orthogonal to) an imaginary straight line which passes through the cover 690 and which is parallel with a straight line connecting the light emitting elements 621 and 622 and the light receiving element 623.

In this embodiment, the thickness of the cover 690 having light transmitting properties is 1 mm, and the depth of the grooves 697 is 0.3 mm. The width of the grooves 697 is 0.3 mm, and the pitch between the grooves 697 is 0.6 mm. That is, in this embodiment, the aspect ratio of a region between the grooves 697 (the ratio of the depth of the grooves 697 to the distance between the grooves 697) is set to be 1 (see FIG. 17).

It is preferable that the aspect ratio of a region between the grooves 697 is about 1 to 2. The reason for this is as follows. Light striking the lateral surfaces of the grooves 697 is radiated to the exterior (that is, the amount of stray light is reduced), while light striking the bottom surfaces of the grooves 597 is reflected inward and returns. That is, if the aspect ratio is decreased (if the depth of the grooves 697 is decreased), the amount of light which is reflected and returns is increased. However, if the aspect ratio is excessively increased, it makes it difficult for light to enter the grooves 697. Thus, it is desirable to set the aspect ratio of the grooves 697 to a value which makes it possible for light to enter the grooves 697 and also makes it easier for light to strike the lateral surfaces of the grooves 697. The grooves 697 may be machined roughly.

The detection of biological information by using the biosensor 600 is performed by allowing a part of a body, for example, a fingertip of a left hand of a patient, to contact the biosensor 600.

When detecting biological information, light emitted from the light emitting elements 621 and 622 passes through the light-emitting-element sealing portion 671 and impinges on the cover 690 through the opening 671a. Light then passes through the cover 690 and impinges on the fingertip.

Light incident on and passing through the fingertip further passes through the cover 690 and impinges on the opening 672a of the light-receiving-element sealing portion 672. Then, light passes through the light-receiving-element sealing portion 672 and is received by the light receiving element 623. With this operation, a change in the intensity of light passing through the fingertip is obtained as a photoplethysmographic signal. In this case, since light beams of different wavelengths are emitted from the two light emitting elements 621 and 622, the intensity of the transmitted light concerning the two wavelengths can be obtained.

The cover 690 having light transmitting properties is disposed between the light emitting elements 621 and 622 and the fingertip 12. Accordingly, part of light emitted from the light emitting elements 621 and 622 enters the cover 690 and propagates through the cover 690 toward the light receiving element 623. In this biosensor 600, the plurality of grooves 697 are formed on the bottom surface 690a of the cover 690. Accordingly, as shown in FIG. 17, light (stray light) entering the cover 690 strikes the lateral surfaces of the plurality of grooves 697 when advancing within the cover 690 while being reflected, and is radiated from the lateral surfaces to the exterior. Accordingly, the amount of stray light which enters the light receiving element 623 is reduced.

As discussed above in detail, in the biosensor 600 according to this embodiment, when a fingertip contacts the front surface of the biosensor 600, light emitted from the light emitting elements 621 and 622 impinges on the fingertip via the light-emitting-element sealing portion 671 and the cover 690. Then, light passing through the fingertip is received by the light receiving element 623 via the cover 690 and the light-receiving-element sealing portion 672. With this operation, a photoplethysmographic signal indicating a pulse wave of the fingertip 12 is obtained.

In the biosensor 600, the light shielding portion 673 is disposed between the light-emitting-element sealing portion 671 and the light-receiving-element sealing portion 672. Accordingly, light emitted from the light emitting elements 621 and 622 is blocked from directly impinging on the light receiving element 623 by the provision of the light shielding portion 673. Meanwhile, part of light emitted from the light emitting elements 621 and 622 enters the cover 690 and propagates through the cover 690 toward the light receiving element 623. In this biosensor 600, however, the plurality of grooves 697 are formed on the bottom surface of the cover 690. Accordingly, light (stray light) which has entered the cover 690 strikes the lateral surfaces of the plurality of grooves 697 when advancing within the cover 690 while being reflected, and is then radiated from the lateral surfaces to the exterior, thereby reducing the amount of stray light which enters the light receiving element 623. As a result, in the biosensor 600 which obtains a photoplethysmographic signal, it is possible to reduce the amount of stray light which is received without passing through a body.

In particular, in this embodiment, the aspect ratio is set to be 1. This makes it easier for light (stray light) to strike the lateral surfaces of the grooves 697, thereby making it possible to further reduce the amount of stray light which enters the light receiving element 623.

The biosensor 600 according to the sixth embodiment has been discussed above. However, the present invention is not restricted to the above-described embodiment, and various modifications may be made. For example, in this embodiment, the plurality of grooves 697 are formed on the back surface (bottom surface) of the cover 690. However, instead of or in addition to the back surface of the cover 690, grooves may be formed on the top surface. The plurality of grooves 697 do not have to be arranged at equal intervals (periodically).

REFERENCE SIGNS LIST 100, 200, 300, 400, 500, 600 biosensor
110, 115, 210, 310, 410, 510, 610 sensor unit
121, 122, 221, 222, 321, 322, 421, 422, 521, 522, 621, 622 light emitting element
123, 223, 323, 423, 523, 623 light receiving element
130, 230, 330 first electrocardiograph electrode
140, 240, 340 second electrocardiograph electrode
150, 157, 250, 350 base medium
160, 260, 360, 460, 560, 660 wiring board
170, 175, 270, 370, 470, 570, 670 sealing section
171, 271, 371, 471, 571, 671 light-emitting-element sealing portion
172, 272, 372, 472, 572, 672 light-receiving-element sealing portion
173, 273, 373, 473, 573, 673 light shielding portion
180, 185, 280, 380 adhesion layer
490, 590, 690 cover
697 groove
14 division direction
15 imaginary straight line

The invention claimed is:

1. A biosensor comprising:
a wiring board;
a light emitting element and a light receiving element disposed on a principal surface of the wiring board;
a light-emitting-element sealer disposed on the principal surface of the wiring board and adjacent to the light emitting element to seal the light emitting element;
a light-receiving-element sealer disposed on the principal surface of the wiring board and adjacent to the light emitting element to seal the light receiving element;
a light shielding portion disposed between the light-emitting-element sealer and the light-receiving-element sealer; and
a cover with light transmitting properties disposed in parallel with the wiring board with the light emitting element, the light receiving element and the light shielding portion disposed therebetween,
wherein the cover comprises a roughened bottom surface that faces towards the light emitting element and the light receiving element and that is configured to scatter light passing through the cover.

2. The biosensor according to claim 1, wherein the light emitting element comprises a pair of light emitting devices configured to emit light beams at different wavelengths.

3. The biosensor according to claim 1, wherein the light-emitting-element sealer and the light-receiving-element sealer each comprise a circular truncated cone shape that surrounds the light emitting element and the light receiving element, respectively.

4. The biosensor according to claim 1, wherein the cover is at least partially divided into a first portion adjacent to the light emitting element and a second portion adjacent to the light receiving element.

5. The biosensor according to claim 1, wherein the roughened bottom surface of the cover does not extend to cover the light emitting element and the light receiving element in a direction normal thereto.

6. A biosensor comprising:
a wiring board;
a light emitting element and a light receiving element disposed on a principal surface of the wiring board;
a light-emitting-element sealer disposed on the principal surface of the wiring board and adjacent to the light emitting element to seal the light emitting element;
a light-receiving-element sealer disposed on the principal surface of the wiring board and adjacent to the light emitting element to seal the light receiving element;
a light shielding portion disposed between the light-emitting-element sealer and the light-receiving-element sealer; and
a cover with light transmitting properties disposed in parallel with the wiring board with the light emitting element, the light receiving element and the light shielding portion disposed therebetween,
wherein the cover is at least partially divided such that an angle between a direction in which the cover is partially divided and a straight line connecting the light emitting element and the light receiving element in a plane parallel to the principal surface of the wiring board is less than or equal to 50°.

7. The biosensor according to claim 6, wherein the light emitting element comprises a pair of light emitting devices configured to emit light beams at different wavelengths.

8. The biosensor according to claim 6, wherein the light-emitting-element sealer and the light-receiving-element sealer each comprise a circular truncated cone shape that surrounds the light emitting element and the light receiving element, respectively.

9. The biosensor according to claim 6, wherein the cover is at least partially divided into a first portion adjacent to the light emitting element and a second portion adjacent to the light receiving element.

10. A biosensor comprising:
- a wiring board;
- a light emitting element and a light receiving element disposed on a principal surface of the wiring board;
- a light-emitting-element sealer disposed on the principal surface of the wiring board and adjacent to the light emitting element to seal the light emitting element;
- a light-receiving-element sealer disposed on the principal surface of the wiring board and adjacent to the light emitting element to seal the light receiving element;
- a light shielding portion disposed between the light-emitting-element sealer and the light-receiving-element sealer; and
- a cover with light transmitting properties disposed in parallel with the wiring board with the light emitting element, the light receiving element and the light shielding portion disposed therebetween,
- wherein the cover is fully divided such that an angle between a direction extending parallel to a division region where the cover is divided and a straight line connecting the light emitting element and a light receiving element in a plane parallel to the principal surface of the wiring board is less than or equal to 50°.

11. The biosensor according to claim 10, wherein the light emitting element comprises a pair of light emitting devices configured to emit light beams at different wavelengths.

12. The biosensor according to claim 10, wherein the light-emitting-element sealer and the light-receiving-element sealer each comprise a circular truncated cone shape that surrounds the light emitting element and the light receiving element, respectively.

13. The biosensor according to claim 10, wherein the cover is at least partially divided into a first portion adjacent to the light emitting element and a second portion adjacent to the light receiving element.

14. A biosensor comprising:
- a wiring board;
- a light emitting element and a light receiving element disposed on a principal surface of the wiring board;
- a light-emitting-element sealer disposed on the principal surface of the wiring board and adjacent to the light emitting element to seal the light emitting element;
- a light-receiving-element sealer disposed on the principal surface of the wiring board and adjacent to the light emitting element to seal the light receiving element;
- a light shielding portion disposed between the light-emitting-element sealer and the light-receiving-element sealer; and
- a cover with light transmitting properties disposed in parallel with the wiring board with the light emitting element, light receiving element and the light shielding portion therebetween,
- wherein the cover comprises a bottom surface having a plurality of grooves that face towards the light emitting element and the light receiving element.

15. The biosensor according to claim 14, wherein the plurality of grooves extend in a direction intersecting an imaginary straight line that passes through the cover and that is parallel with a straight line connecting the light emitting element and the light receiving element.

16. The biosensor according to claim 15, wherein an aspect ratio of a region between the grooves is greater than or equal to 1.

17. The biosensor according to claim 14, wherein the light emitting element comprises a pair of light emitting devices configured to emit light beams at different wavelengths.

18. The biosensor according to claim 14, wherein the light-emitting-element sealer and the light-receiving-element sealer each comprise a circular truncated cone shape that surrounds the light emitting element and the light receiving element, respectively.

19. The biosensor according to claim 14, wherein the cover is at least partially divided into a first portion adjacent to the light emitting element and a second portion adjacent to the light receiving element.

20. The biosensor according to claim 14, wherein the plurality of grooves of the bottom surface do not extend to cover the light emitting element and the light receiving element in a direction normal thereto.

* * * * *